United States Patent
Takeuchi et al.

(10) Patent No.: US 11,412,579 B2
(45) Date of Patent: Aug. 9, 2022

(54) BATTERY UNIT, FLAVOR INHALER, METHOD OF CONTROLLING BATTERY UNIT, AND PROGRAM

(71) Applicant: JAPAN TOBACCO INC., Tokyo (JP)

(72) Inventors: Manabu Takeuchi, Tokyo (JP); Takaya Takahashi, Tokyo (JP); Manabu Yamada, Tokyo (JP); Hajime Fujita, Tokyo (JP)

(73) Assignee: JAPAN TOBACCO INC., Tokyo (JP)

(*) Notice: Subject to any disclaimer, the term of this patent is extended or adjusted under 35 U.S.C. 154(b) by 139 days.

(21) Appl. No.: 16/878,623

(22) Filed: May 20, 2020

(65) Prior Publication Data

US 2020/0275704 A1 Sep. 3, 2020

Related U.S. Application Data

(63) Continuation of application No. 16/554,226, filed on Aug. 28, 2019, now Pat. No. 11,202,342, which is a
(Continued)

(51) Int. Cl.
*H05B 1/02* (2006.01)
*H05B 3/42* (2006.01)
(Continued)

(52) U.S. Cl.
CPC ............ *H05B 1/0227* (2013.01); *A24F 40/46* (2020.01); *A24F 40/50* (2020.01); *A24F 40/53* (2020.01);
(Continued)

(58) Field of Classification Search
CPC ......... H05B 1/0227; H05B 3/42; A24F 40/46; A24F 40/50; A24F 40/53; A24F 40/10;
(Continued)

(56) References Cited

U.S. PATENT DOCUMENTS

| | | |
|---|---|---|
| 6,040,560 A | 3/2000 | Fleischhauer et al. |
| 7,521,896 B2 | 4/2009 | Yudahira et al. |

(Continued)

FOREIGN PATENT DOCUMENTS

| | | |
|---|---|---|
| CN | 1652427 A | 8/2005 |
| CN | 203434232 U | 2/2014 |

(Continued)

OTHER PUBLICATIONS

Extended European search report dated Oct. 2, 2020, in corresponding European patent Application No. 17900224.1, 9 pages.
(Continued)

*Primary Examiner* — Michael C Zarroli
(74) *Attorney, Agent, or Firm* — Xsensus LLP

(57) ABSTRACT

Provided is a battery unit including: a power supply; a detector configured to detect an output voltage of the power supply; a connecting configured to be connectable with a load for atomizing an aerosol source or heating a flavor source; and a controller capable of executing a power supply mode in which electric power is supplied to the load from the power supply. The controller executes a specific control different from the supply of electric power to the load based on am amount of change in the output voltage per a predetermined time period in the power supply mode.

9 Claims, 13 Drawing Sheets

Related U.S. Application Data continuation of application No. PCT/JP2017/008858, filed on Mar. 6, 2017.

(51) Int. Cl.
*A24F 40/50* (2020.01)
*A24F 40/10* (2020.01)
*H02J 7/00* (2006.01)
*A24F 40/46* (2020.01)
*A24F 40/53* (2020.01)
*A61M 11/04* (2006.01)
*A24F 40/90* (2020.01)

(52) U.S. Cl.
CPC ......... *A61M 11/042* (2014.02); *H02J 7/0063* (2013.01); *H02J 7/0068* (2013.01); *H05B 3/42* (2013.01); *A24F 40/10* (2020.01); *A24F 40/90* (2020.01); *A61M 2205/8206* (2013.01)

(58) Field of Classification Search
CPC ........ A24F 40/90; A24F 47/00; H02J 7/0063; H02J 7/0068; H02J 7/007188; H02J 7/0031; H02J 7/0036; H02J 7/0047
See application file for complete search history.

(56) References Cited

U.S. PATENT DOCUMENTS

| | | | |
|---|---|---|---|
| 10,524,508 | B2 | 1/2020 | Sur et al. |
| 10,993,474 | B2 | 5/2021 | Matsumoto et al. |
| 2014/0254055 | A1 | 9/2014 | Xiang |
| 2014/0270727 | A1 | 9/2014 | Ampolini et al. |
| 2014/0283856 | A1 | 9/2014 | Xiang |
| 2014/0305454 | A1 | 10/2014 | Rinker et al. |
| 2015/0036250 | A1 | 2/2015 | Xiang |
| 2015/0128976 | A1 | 5/2015 | Verleur et al. |
| 2015/0305409 | A1 | 10/2015 | Verleur et al. |
| 2016/0089508 | A1* | 3/2016 | Smith ............... A24F 40/65 128/200.16 |
| 2016/0174076 | A1 | 6/2016 | Wu |
| 2016/0345627 | A1 | 12/2016 | Liu |
| 2016/0360785 | A1* | 12/2016 | Bless ............... A24F 40/70 |
| 2016/0374397 | A1 | 12/2016 | Jordan et al. |
| 2017/0013879 | A1 | 1/2017 | Frisbee et al. |
| 2017/0018819 | A1 | 1/2017 | Toya et al. |
| 2017/0042251 | A1 | 2/2017 | Yamada et al. |
| 2017/0042252 | A1 | 2/2017 | Takeuchi et al. |
| 2017/0231285 | A1 | 8/2017 | Holzherr et al. |
| 2019/0058970 | A1 | 2/2019 | Baker et al. |
| 2021/0177054 | A1 | 6/2021 | Zitzke |
| 2021/0178093 | A1 | 6/2021 | Frisbee et al. |

FOREIGN PATENT DOCUMENTS

| | | | |
|---|---|---|---|
| CN | 204120221 U * | 1/2015 | |
| CN | 105636466 A | 6/2016 | |
| EP | 1562273 A2 | 8/2005 | |
| EP | 2 927 703 A1 | 10/2015 | |
| EP | 2966743 A1 | 1/2016 | |
| EP | 3039971 A1 | 7/2016 | |
| EP | 3042576 A1 | 7/2016 | |
| GB | 2 510 821 A | 8/2014 | |
| JP | H09-329651 A | 12/1997 | |
| JP | 11-507718 A | 7/1999 | |
| JP | 2003-317811 A | 11/2003 | |
| JP | WO 2014-501106 A | 1/2014 | |
| JP | 2014-527835 A | 10/2014 | |
| JP | 2015-001411 A | 1/2015 | |
| JP | 2016-514443 A | 5/2016 | |
| JP | 2016-517270 A | 6/2016 | |
| RU | 2707794 C2 | 11/2019 | |
| WO | WO 96/39879 A1 | 12/1996 | |
| WO | WO 2012/085205 A1 | 6/2012 | |
| WO | 2014/083756 A1 | 6/2014 | |
| WO | 2014/124996 A1 | 8/2014 | |
| WO | 2014/150247 A1 | 9/2014 | |
| WO | WO 2015/166952 A1 | 11/2015 | |
| WO | WO 2015/167000 A1 | 11/2015 | |
| WO | WO 2016/119626 A1 | 8/2016 | |
| WO | 2017/021550 A1 | 2/2017 | |

OTHER PUBLICATIONS

Extended European search report dated Oct. 8, 2020, in corresponding European patent Application No. 17899271.5, 10 pages.
Partial supplementary European search report dated Aug. 11, 2020, in corresponding European patent Application No. 17899394.5, 13 pages.
Office Action dated Aug. 4, 2020, in corresponding Chinese patent Application No. 201780020117.8, 24 pages.
Office Action dated Aug. 28, 2020, in corresponding Eurasian patent Application No. 201992105, 4 pages.
Office Action dated Aug. 28, 2020, in corresponding Eurasian patent Application No. 201992106, 19 pages.
"Power Control from Texas Instruments: Protection, Monitoring, Switching", Jul. 22, 2014, total 20 pages, online article: https://www.comnel.ru/lib/61888.
Japanese Office Action dated Nov. 9, 2020, in corresponding Japanese Patent Application No. 2018-540497.
Japanese Office Action dated May 28, 2020 ,against the corresponding Japanese Patent Application No. 2018-540497.
Eurasian Office Action dated Apr. 23, 2021, in Eurasian Patent Application No. 201992105.
Eurasian Office Action dated Jun. 7, 2021, in Eurasian Patent Application No. 201992104.
Office Action dated Aug. 14, 2020, in corresponding Chinese patent Application No. 201780020116.3, 40 pages.
Canadian Office Action dated Dec. 2, 2020, in corresponding Canadian Patent Application No. 3,054,273.
International Search Report, issued in PCT/JP2017/008857, dated Apr. 4, 2017.
International Search Report, issued in PCT/JP2017/008858, dated Apr. 4, 2017.
International Search Report, issued in PCT/JP2017/008859, dated Apr. 4, 2017.
Japanese Office Action, issued in Application No. 2018-167923, dated Feb. 7, 2019.
Japanese Office Action, issued in Application No. 2018-167923, dated Oct. 16, 2018.
Office Action dated May 12, 2022, in corresponding U.S. Appl. No. 16/554,292, 45 pp.

* cited by examiner

BATTERY UNIT, FLAVOR INHALER, METHOD OF CONTROLLING BATTERY UNIT, AND PROGRAM

CROSS REFERENCE TO RELATED APPLICATIONS

This application is a Continuation of U.S. application Ser. No. 16/554,226, filed Aug. 28, 2019 (now U.S. Pat. No. 11,202,342), which is Continuation of PCT International Application No. PCT/W2017/008858, filed on Mar. 6, 2017, each of which is hereby expressly incorporated by reference into the present application.

TECHNICAL FIELD

The present invention relates to a battery unit including a connection configured to be connectable with an atomizer for atomizing an aerosol source, a flavor inhaler including the battery unit, a method of controlling the battery unit, and a program for executing the method.

BACKGROUND ART

Instead of cigarettes, non-combustion-type flavor inhalers (electronic cigarettes) for inhaling flavor without combustion have been proposed (see PTLs 1 to 6). The flavor inhaler includes at least one of an aerosol source and a flavor source, an atomizer that is an electric load for atomizing inhaling taste components contained in at least one of the aerosol source and the flavor source, a power supply configured to supply electric power to the atomizer, and a controller configured to control the atomizer and the power supply.

PTL 1 discloses that the atomizer is configured to be detachably connected to the battery unit provided with the power supply and the controller. PTL 1 discloses that the atomizer connected to the battery unit can be identified using identification information such as an ID.

PTL 2 discloses an electronic smoking apparatus in which the atomizer and a charger can be alternatively connected to a common connection (interface) of the battery unit.

PTL 3 discloses that over-current flowing in an electronic circuit in an electronic cigarette or short circuit in the electronic circuit is detected. PTL 4 discloses a fuse that prevents overheating of the atomizer in the electronic cigarette. PTL 5 discloses that when there is a system malfunction in an aerosol generating device such as an electric smoking utensil, the fuse in the electronic circuit is blown, thereby disabling the system. PTL 6 discloses that over-current and over-voltage are detected in a charging process of the battery unit of the electronic cigarette.

PTL 7 discloses a charge monitoring device configured to monitor a charged state of a battery when the battery is charged. This charge monitoring device detects an abnormal charge state by monitoring change in voltage of the battery to be charged with respect to time or change in voltage of the battery to be charged with respect to a charging electric quantity, and also monitoring a voltage value of the battery measured by the voltage measurement means.

PTL 8 discloses a user authentication technique based on the inhaling pressure in a puff action of the user in the flavor inhaler.

PTL 9 discloses a technique in which the flavor inhaler is easily disabled.

CITATION LIST

Patent Literature

PTL 1: U.S. Patent No. 2016/0174076
PTL 2: International Publication No. WO 2016/119626
PTL 3: U.S. Patent No. 2014/0254055
PTL 4: U.S. Patent No. 2014/0283856
PTL 5: National Publication of International Patent Application No. 2014-501106
PTL 6: U.S. Patent No. 2015/0036250
PTL 7: Japanese Patent Laid-Open No. 2003-317811
PTL 8: International Publication No. WO 2015/167000
PTL 9: National Publication of International Patent Application No. H11-507718

SUMMARY OF INVENTION

A first feature is a battery unit, comprising: a power supply; a detector configured to detect an output voltage of the power supply; a connection configured to be connectable with a load for atomizing an aerosol source or heating a flavor source; and a controller capable of executing a power supply mode in which electric power is supplied to the load from the power supply, wherein the controller executes a specific control different from the supply of electric power to the load based on an amount of change in the output voltage per a predetermined time period in the power supply mode.

A second feature is the battery unit according to the first feature, wherein the specific control is authentication of the load.

A third feature is the battery unit according to the second feature, wherein if the amount of change in the output voltage per a predetermined time period is included in a predetermined range, the authentication of the load is continued.

A fourth feature is the battery unit according to the second feature or the third feature, wherein if the amount of change in the output voltage per a predetermined time period is not included in a predetermined range, the authentication of the load is cancelled.

A fifth feature is the battery unit according to the fourth feature, wherein if the authentication of the load is cancelled, the controller determines whether the authentication of the load is performed based on the amount of change in the output voltage per a predetermined time period when a resume operation is detected.

A sixth feature is the battery unit according to any one of the first feature to the fifth feature, wherein the connection is capable of connecting with a charger for charging the power supply and the load, the controller is capable of executing the power supply mode and a charge mode in which the charger charges the power supply, and the specific control is a control for determining an abnormality in the charge mode.

A seventh feature is the battery unit according to the sixth feature, wherein if a decreasing amount of the output voltage per a predetermined time period in the charge mode is equal to or smaller than a first threshold which is set based on the decreasing amount of the output voltage per the predetermined time period in the power supply mode, the controller determines the abnormality in the charge mode.

The eighth feature is the battery unit according to the seventh feature, wherein the first threshold is set to be equal to or smaller than the amount of change in the output voltage per the predetermined time period in the power supply mode.

The ninth feature is the battery unit according to any one of the sixth feature to the eighth feature, comprising a switch that is capable of electrically connecting or disconnecting the power supply to or from the load or the charger that is connected to the connection, wherein the controller turns on the switch if a first condition is satisfied in the power supply mode, and the controller turns on the switch if a second condition different from the first condition is satisfied in the charge mode.

A tenth feature is the battery unit according to the ninth feature, comprising a detector configured to detect an operation for using the load, wherein the first condition is a condition based on detection of the operation.

The eleventh feature is the battery unit according to the ninth feature or the tenth feature, wherein the second condition is a condition based on connection of the charger to the connection.

The twelfth feature is a flavor inhaler, comprising: the battery unit according to any one of the first feature to the eleventh feature; and the load.

A thirteenth feature is a method of controlling a battery unit including a controller that is capable of executing a power supply mode in which electric power is supplied to a load from a power supply through a connection configured to be connectable with the load for atomizing an aerosol source or heating a flavor source, the method comprising the steps of: detecting an output voltage of the power supply; and executing a specific control different from the supply of electric power to the load based on an amount of change in the output voltage per a predetermined time period in the power supply mode.

The fourteenth feature is a program causing a battery unit to execute the method according to the thirteenth feature.

Here, the description made in the scope of claims will be complemented as below. The description reading that "the decreasing amount of the output voltage per a predetermined time period" means an amount representing how much the output voltage is decreased in a predetermined time period. In other words, the decreasing amount is an amount representing how small the output voltage at the end of the predetermined time period is with respect to the output voltage at the start of the time period. For example, the "decreasing amount of the output voltage per a predetermined time period" is obtained by subtracting the output voltage at the start of the predetermined time period from the output voltage at the end of the predetermined time period. When the "decreasing amount of the output voltage per a predetermined time period" has a negative value, the output voltage is decreased in the predetermined time period. On the other hand, when the "decreasing amount of the output voltage per a predetermined time period" has a positive value, the output voltage is increased in the predetermined time period. Note that when two "decreasing amounts of the output voltage per a predetermined time period" that are different from each other are compared, smaller "decreasing amount of the output voltage per a predetermined time period" means that the output voltage is more greatly decreased in the predetermined time period, in other words, that the output voltage at the end of the predetermined time period is smaller than the output voltage at the start of the predetermined time period.

DESCRIPTION OF EMBODIMENTS

Hereinafter, embodiments will be described. Note that the same or similar parts are denoted by the same or similar reference signs in the descriptions of the drawings below. It should be noted that the drawings are schematic and each ratio in dimensions may be different from an actual ratio.

Therefore, specific dimensions and the like should be determined with reference to the following descriptions. Needless to say, parts in which the relationship or ratio in dimensions varies between the mutual drawings, may be included.

[Outline of Disclosure]

A flavor inhaler such as an electronic cigarette includes an electric load for atomizing an aerosol source or heating a flavor source. The electric load is configured to atomize the aerosol source or heat the flavor source using electric power supplied from a power supply. Since the electric power from the power supply is supplied to the electric load electrically connected in an electronic circuit in the flavor inhaler, an output voltage of the power supply decreases. The inventors of the present invention have focused on the fact that an amount of change in the output voltage changes according to the specification of the electric load, and have found that the amount of change in the output voltage of the power supply can be effectively used for the control of the battery unit and the flavor inhaler.

According to the outline of the disclosure, the battery unit includes a power supply; a detector configured to detect an output voltage of the power supply; a connection configured to be connectable with a load for atomizing an aerosol source or heating a flavor source; and a controller capable of executing a power supply mode in which electric power is supplied to the load from the power supply, wherein the controller executes, based on an amount of change in the output voltage per a predetermined time period in the power supply mode, a specific control different from the supply of electric power to the load.

First Embodiment (Non-Combustion-Type Flavor Inhaler)

Figure 1:
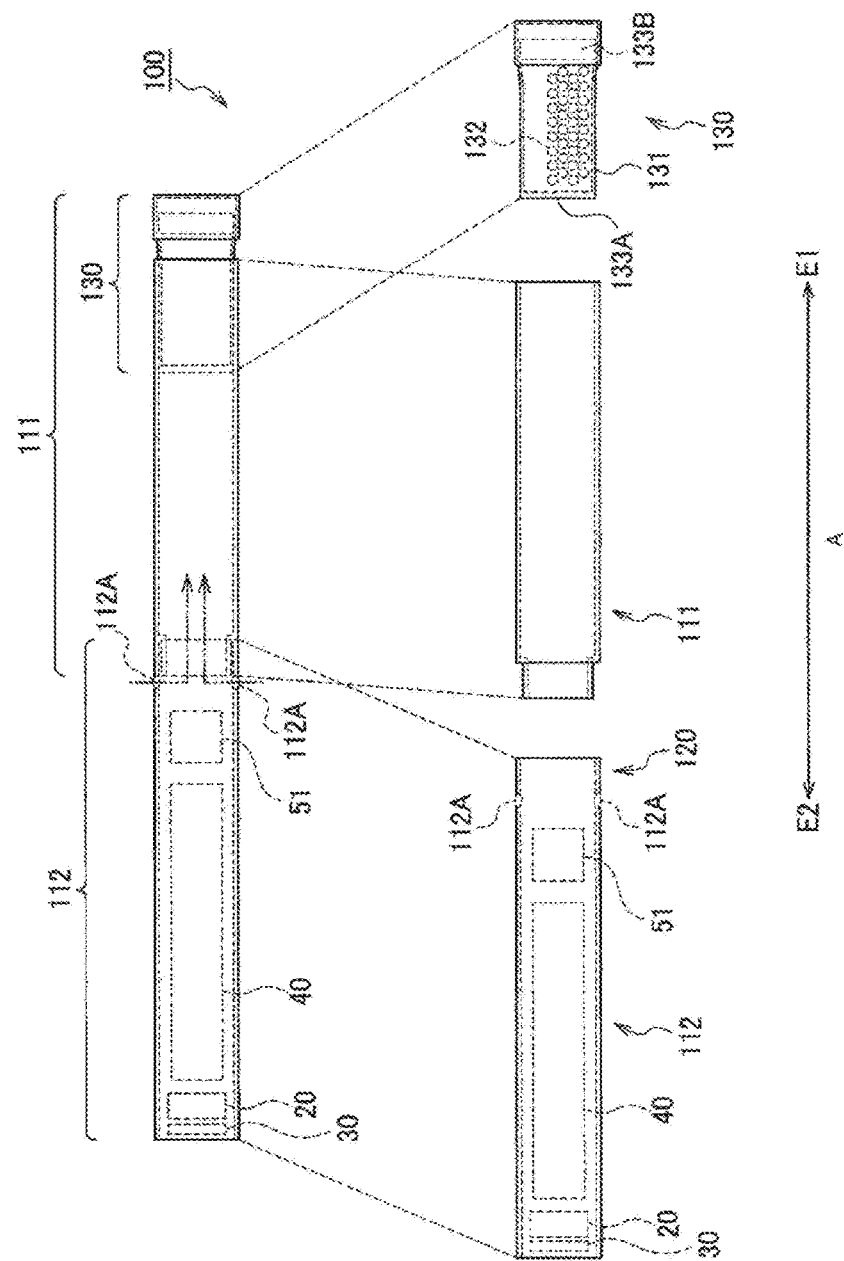
FIG. 1 is an exploded view illustrating a flavor inhaler according to one embodiment.
Figure 2:
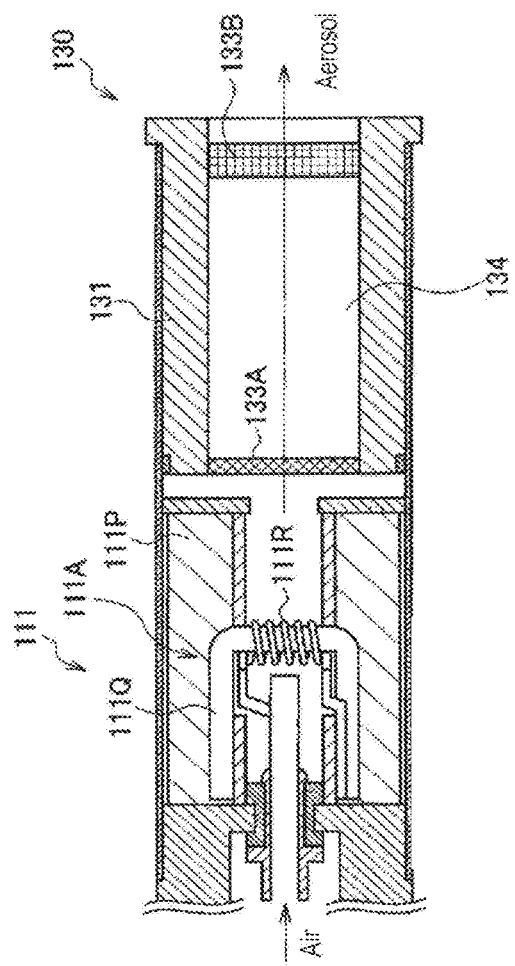
FIG. 2 is a diagram illustrating an atomizing unit according to one embodiment.
Figure 3:
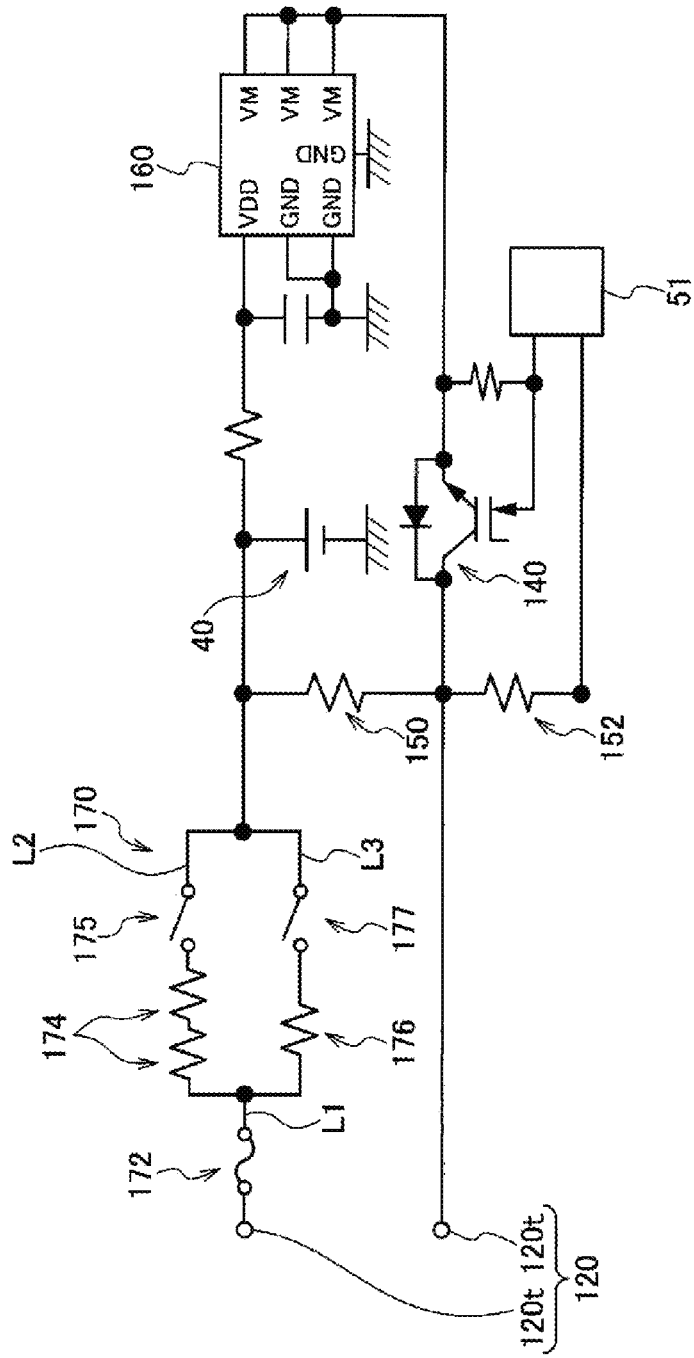
FIG. 3 is a diagram illustrating an electric circuit provided in a battery unit.
Figure 4:
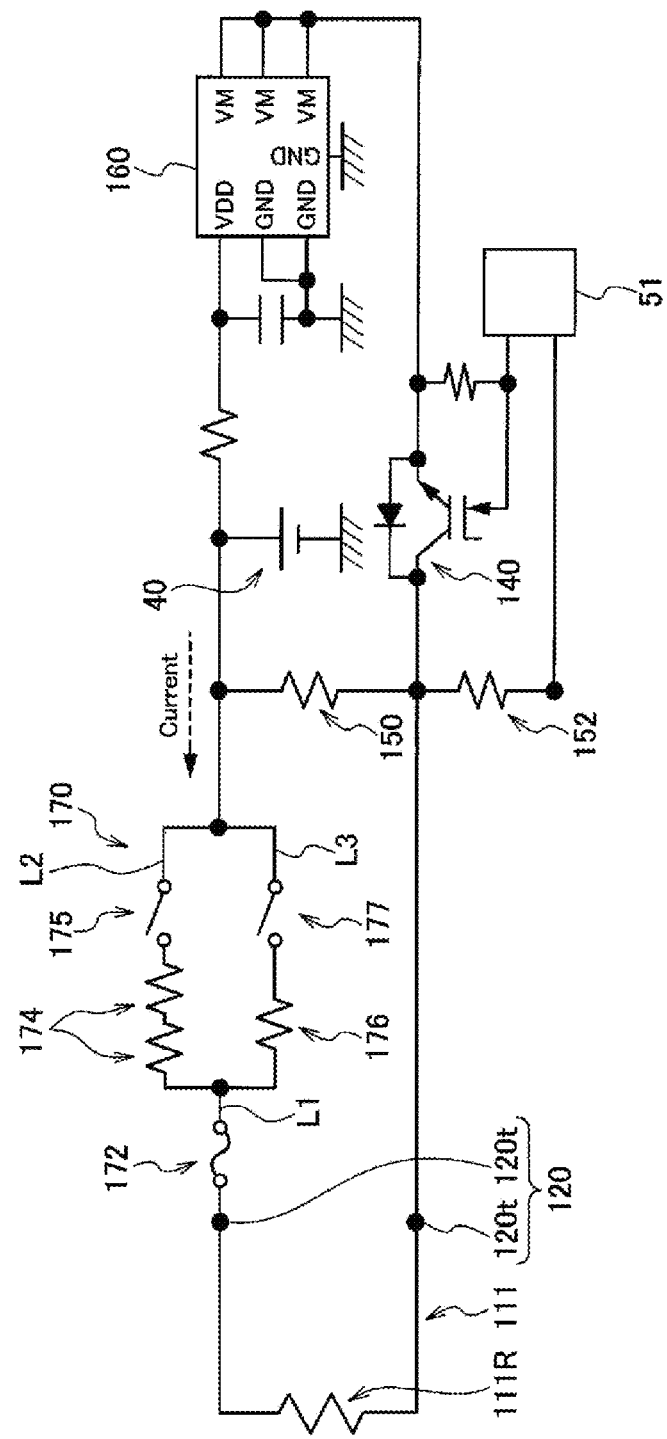
FIG. 4 is a diagram illustrating an electric circuit including the atomizing unit and the battery unit in a state in which a load is connected to the battery unit.
Figure 5:
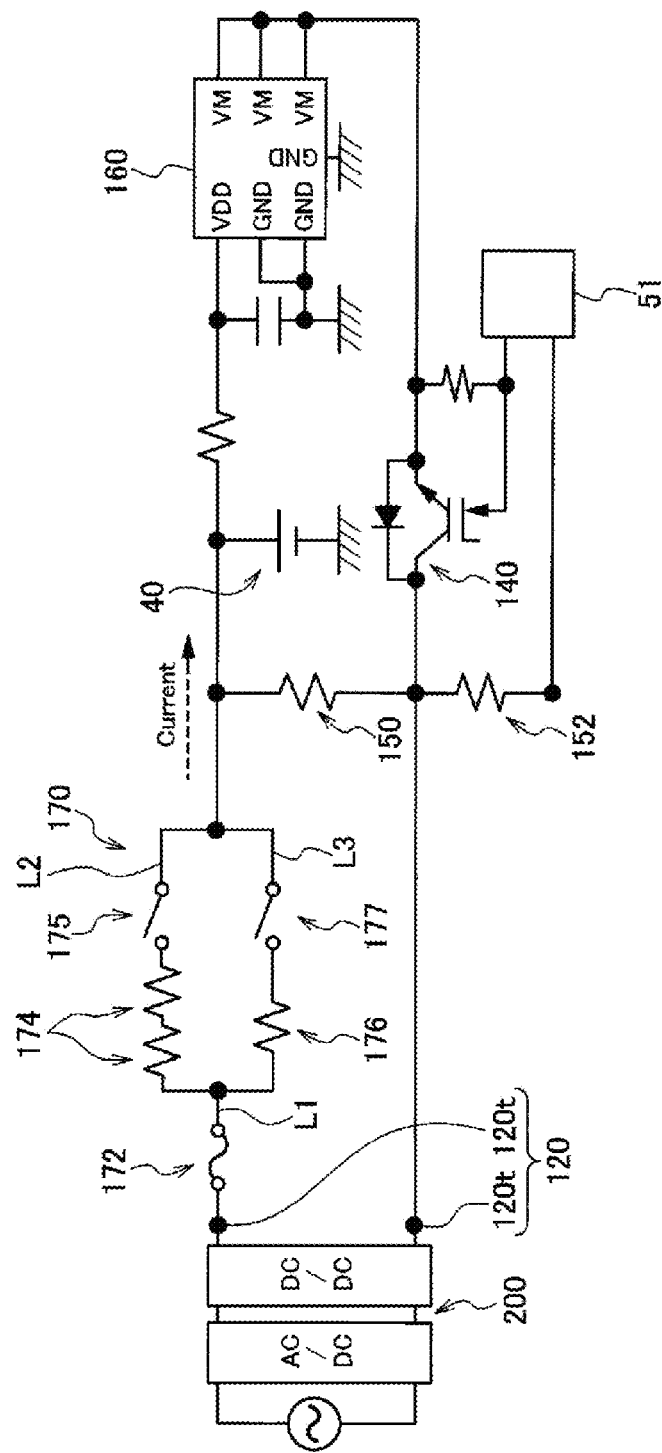
FIG. 5 is a diagram illustrating an electric circuit including a charger and the battery unit in a state in which the charger is connected to the battery unit.

Hereinafter, a flavor inhaler according to a first embodiment will be described. FIG. 1 is an exploded view illustrating a flavor inhaler according to one embodiment. FIG. 2 is a diagram illustrating an atomizing unit according to one embodiment. FIG. 3 is a diagram illustrating an electric circuit provided in a battery unit. FIG. 4 is a diagram illustrating an electric circuit including a load and the battery unit in a state in which the load is connected to the battery unit. FIG. 5 is a diagram illustrating an electric circuit including a charger and the battery unit in a state in which the charger is connected to the battery unit.

A flavor inhaler 100 may be a non-combustion-type flavor inhaler with which a user inhales an inhalation component (inhaling taste component) without combustion. The flavor inhaler 100 may have a shape extending in a predetermined direction A that is a direction toward a mouthpiece end E1 from a non-mouthpiece end E2.

The flavor inhaler 100 may include a battery unit 112 and an atomizing unit 111. The atomizing unit 111 may include an aerosol source that generates aerosol and/or a flavor source that generates a flavor component, and an electric load 111R for atomizing the aerosol source or heating the flavor source. It is sufficient that the load 111R is an element that can generate aerosol and/or a flavor component from the aerosol source and/or the flavor source by receiving the electric power.

The battery unit 112 includes a power supply 40 and a controller 51. The power supply 40 stores the electric power necessary for the operation of the flavor inhaler 100. The power supply 40 supplies the electric power to the load of an atomization assembly 120. The power supply 40 may be, for example, a rechargeable battery such as a lithium ion battery.

The battery unit 112 includes a connection 120 configured to be connectable with the load 111R of the atomizing unit 111 or a charger 200 for charging the power supply 40. The connection 120 of the battery unit 112 is configured to be alternatively connectable with the load 111R and the charger 200. In other words, the charger 200 or the load 111R is exclusively connected to the connection 120 of the battery unit 112, and the charger 200 and the load 111R are not connected to the connection 120 at the same time. However, this does not apply to a case in which the battery unit 112 includes a plurality of connections 120.

The connection 120 of the battery unit 112 includes electric terminals 120t for being electrically connected with the load 111R of the atomizing unit 111 and the charger 200. The electric terminals 120t are connected to the power supply 40 and the controller 51 (see FIG. 3).

When the atomizing unit 111 is connected to the connection 120 of the battery unit 112, the load 111R provided in the atomizing unit 111 is connected to the power supply 40 of the battery unit 112 through the electric terminals 120t (see FIG. 4). When the charger 200 is connected to the connection 120 of the battery unit 112, the charger 200 is electrically connected to the power supply 40 of the battery unit 112 through the electric terminals 120t (see FIG. 5).

The battery unit 112 may include an inlet hole 112A through which air flows in from outside. The air that has flowed in through the inlet hole 112A reaches a mouthpiece provided in the mouthpiece end E1 of the flavor inhaler 100 through a flow path provided inside of the atomizing unit 111. Note that another inlet hole may be provided in the atomizing unit 111, instead of the inlet hole 112A or to be used together with the inlet hole 112A. As another variation, the atomizing unit 111 and the battery unit 112 may be configured so that the inlet hole is formed in the connection portion (boundary portion) when the atomizing unit 111 is connected to the battery unit 112.

Hereinafter, a detailed example of the atomizing unit 111 will be described with reference to FIG. 1 and FIG. 2. The atomizing unit 111 may include a reservoir 111P, a wick 111Q, and the load 111R. The reservoir 111P stores a liquid aerosol source. The reservoir 111P may be a porous body formed by, for example, materials such as a resin web. The wick 111Q is a liquid holding member for drawing the aerosol source from the reservoir 111P using capillary action. The wick 111Q is formed by, for example, glass fiber or porous ceramic.

The load 111R may be a resistance heating element. This resistance heating element atomizes the aerosol source held by the wick 111Q. For example, the resistance heating element is formed by a resistance heating element (e.g., heating wire) wound around the wick 111Q.

The air that has flowed from the inlet hole 112A passes through the vicinity of the load 111R in the atomizing unit 111. The aerosol generated by the load 111R flows together with the air toward the mouthpiece.

The aerosol source may be a liquid at ordinary temperatures. For example, polyhydric alcohol may be used as the aerosol source. The aerosol source itself may contain the flavor component. Alternatively, the aerosol source may include a tobacco material that emits a fragrance inhaling taste component by being heated or an extract deriving from the tobacco material.

Note that in the above-described embodiment, an example of the liquid aerosol source at ordinary temperatures has been described in detail, but instead of the liquid aerosol source, an aerosol source that is a solid at ordinary temperatures may be also used.

The atomizing unit 111 may include a replaceable flavor unit 130. The flavor unit 130 may include a cylindrical body 131, a flavor source 132, a mesh 133A, and a filter 133B. The cylindrical body 131 has a cylindrical shape extending in the predetermined direction A. The cylindrical body 131 includes a retainer 134 that retains the flavor source 132.

The flavor source 132 is provided in a position closer to the mouthpiece side than the atomizing unit 111 in the flow path of the air inhaled from the mouthpiece. The flavor source 132 provides the aerosol atomized by the load 111R of the atomizing unit 111 with fragrance inhaling taste. The flavor added to the aerosol by the flavor source 132 is supplied to the mouthpiece of the flavor inhaler 100.

The flavor source 132 may be a solid at ordinary temperatures. By way of example, the flavor source 132 comprises an ingredient piece of a plant material which provides aerosol with fragrance inhaling taste component. Shredded tobacco or a product, which is made by processing a tobacco material such as a tobacco row material to have a granular form, may be used as an ingredient piece which is a component of the flavor source 132. In this regard, the flavor source 132 may comprise a product which is made by processing a tobacco material to have a sheet form. Also, the ingredient piece, which is a component of the flavor source 132, may comprise a plant (for example, mint, a herb, and the like) other than tobacco. The flavor source 132 may be provided with flavor such as menthol.

The mesh 133A is provided to cover an opening of the cylindrical body 131 on the non-mouthpiece side with respect to the flavor source 132. The filter 133B is provided to cover an opening of the cylindrical body 131 on the mouthpiece side with respect to the flavor source 132. The mesh 133A has a degree of coarseness that is sufficient to prevent the ingredient piece, which is a component of the flavor source 132, from passing through the mesh 133A. The filter 133B is formed by a material having ventilation. The filter 133B has a degree of coarseness that is sufficient to prevent the ingredient piece, which is a component of the flavor source 132, from passing through the filter 133B.

In the present embodiment, the atomizing unit 111 includes both of the aerosol source and the flavor source. Alternatively, the atomizing unit 111 may include only at least one of the aerosol source and the flavor source.

In the present embodiment, since the user of the flavor inhaler 100 places his/her mouth over a portion in the vicinity of the filter 113B to inhale the aerosol, the flavor unit 130 serves as a so-called mouthpiece. Alternatively, another mouthpiece may be provided separately from the flavor unit 130.

In the present embodiment, the load 111R is provided as an element for atomizing the aerosol source. Alternatively, the load 111R may be provided as an element for heating the flavor source 132. In addition, the load 111R may be provided as an element for atomizing the aerosol source and heating the flavor source 132.

In the present embodiment, the load 111R is provided in the vicinity of the reservoir 111P that stores the aerosol source. Alternatively, the load 111R may be provided in the vicinity of the flavor unit 130 that stores the flavor source 132. The number of load 111R is not limited to one, and therefore the loads 111R may be provided in the vicinity of the reservoir 111P and the flavor unit 130, respectively.

The load 111R is not limited to the resistance heating element. It is sufficient that the load 111R is an element that can atomize the aerosol source or heat the flavor source. The load 111R may be, for example, a heat generating element such as a heater or an element such as an ultrasound generator. Examples of the heat generating element include a heat generation resistor, a ceramic heater, and an induction heating type heater.

Next, a specific example of a configuration of the battery unit 112 will be described. The battery unit 112 includes a switch 140 that can electrically connect or disconnect the power supply 40 to or from the load 111R or the charger 200 that is connected to the connection 120. The switch 140 is opened or closed by the controller 51. The switch 140 is formed by, for example, a MOSFET.

When the switch 140 is turned on in a state in which the load 111R is connected to the connection 120, the electric power is supplied to the load 111R from the power supply 40 (see FIG. 4). When the switch 140 is turned on in a state in which the charger 200 is connected to the connection 120, the power supply 40 is charged by the charger 200 (see FIG. 5).

The battery unit 112 includes a determining section that determines whether the charger 200 is connected to the connection 120. The determining section may be a means for determining whether the charger is connected to the connection 120 based on the potential difference between the electric terminals 120t provided to the connection 120. In the present embodiment, the determining section includes a pair of electric resistors 150 and 152 that are arranged in series. One electric resistor 150 of the pair of electric resistors is provided at a position where the connection terminals 120t are connected to each other. The other electric resistor 152 of the pair of electric resistors is connected to one terminal of a control module forming the controller 51.

The pair of electric resistors 150 and 152 may have a known electric resistance value. The electric resistance value of the pair of electric resistors 150 and 152 is sufficiently larger than that of the load 111R, and may be, for example, 10 kΩ.

A potential at a point between the pair of electric resistors 150 and 152 in a state in which nothing is connected to the electric terminals 120t differs from that in a state in which the charger 200 is connected to the electric terminals 120t. Accordingly, the controller 51 can estimate that the connection 120 is connected with nothing or with the charger 200 based on a signal (hereinafter, referred to as a "WAKE signal") received from the other electric resistor 152 of the pair of electric resistors. More specifically, the controller 51 can estimate that the charger 200 is not connected to the connection 120 when detecting a first level (for example, HIGH) WAKE signal. The controller 51 can estimate that the charger 200 is connected to the connection 120 when detecting a second level (for example, LOW) WAKE signal.

A difference between a WAKE signal in the case where the load 111R is connected to the connection 120 and a WAKE signal in the case where the charger 200 is connected to the connection 120 will be described in more detail.

When the switch 140 is turned off and the charger 200 is not connected to the connection 120 as illustrated in FIG. 3, a dark current discharged as stand-by power from the power supply 40 flows through the electric resistors 150 and 152. The controller 51 detects voltage drop between the electric resistors 150 and 152 at that time as the first level WAKE signal.

On the other hand, when the charger 200 is connected to the connection 120 as illustrated in FIG. 5, the current supplied from the charger 200 to charge the power supply 40 preferentially flows to the power supply 40 having a lower resistance value than that of the electric resistor 150 in a parallel circuit of the electric resistor 150 and the power supply 40. Since the potential at the terminal of the electric resistor 152 which is connected with the electric resistor 150 is decreased to approximately ground level, the voltage drop hardly occurs at the electric resistor 152, and the controller 51 detects the second level WAKE signal.

The first level WAKE signal and the second level WAKE signal may have values having a predetermined range which do not overlap each other.

In the present embodiment, the determining section determines whether the charger 200 is connected to the connection 120. Alternatively, the determining section may determine that the connection 120 is in the state of being not connected with any of the charger 200 or the load 111R, in the state of being connected with the charger 200, or in the state of being connected with the load 111R. The WAKE signals detected by the controller 51 in the three states, respectively, are different in level, by increasing the electric resistance value of the load 111R to be sufficiently larger than that of the electric resistor 150.

When the switch 140 is turned off and the load 111R is connected to the connection 120 as illustrated in FIG. 4, a current discharged from the power supply 40 preferentially flows through the load 111R having a lower resistance value than that of the electric resistor 150 in a parallel circuit of the load 111R and the electric resistor 150, and then flows through the electric resistor 152. The controller 51 detects voltage drop between the load 111R and the electric resistor 152 at that time as the third level WAKE signal which does not overlap with the first level WAKE signal and the second level WAKE signal.

The battery unit 112 may include a detector 160 configured to detect an output voltage of the power supply 40. The detector 160 may be provided in the electric circuit in the battery unit 112. The detector 160 may be formed by any well-known electric module. In the present embodiment, the controller 51 and the detector 160 are formed by different modules. Alternatively, the controller 51 and the detector 160 may be formed by one module.

The battery unit 112 may include a disconnecting means 170 for at least temporarily disabling the supply of electric power to the load 111R from the power supply 40. The disconnecting means 170 may be provided between the power supply 40 and the electric terminal 120t in the electric circuit of the battery unit 112.

The disconnecting means 170 is preferably configured to be switchable between a first mode in which the supply of electric power to the load 111R from the power supply 40 is temporarily disabled so that the controller 51 can resume the supply of electric power and a second mode in which the supply of electric power to the load 111R from the power supply 40 is irreversibly disabled so that the controller 51 cannot resume the supply of electric power. The controller 51 may be configured to be able to control the disconnecting means 170 for switching between the first mode and the second mode.

As an example of a specific configuration, the disconnecting means 170 may include a fuse 172. The disconnecting means 170 may be configured so that a normal line L2 and an abnormal line L3 are branched in parallel from a line L1 provided with the fuse 172. In the normal line L2, a first electric resistor 174 and a first switch 175 may be connected in series to each other. In the abnormal line L3, a second electric resistor 176 and a second switch 177 may be connected in series to each other.

When both of the first switch 175 and the second switch 177 are turned off, the electric power cannot be supplied to the load 111R from the power supply 40, and the power supply 40 cannot be charged by the charger 200. During the normal operation, that is, while the abnormal circumstance does not occur, the first switch 175 is turned on and the second switch 177 is turned off. In this way, the load 111R or the charger 200 that is connected to the connection 120 is connected with the power supply 40 through the normal line L2.

In the first mode, both of the first switch 175 and the second switch 177 are turned off. Hereby, the load 111R connected to the connection 120 is electrically disconnected from the power supply 40, thereby temporarily disabling the supply of electric power to the load 111R from the power supply 40.

In the second mode, both of the first switch 175 and the second switch 177 are turned on. Hereby, the current flows in both of the normal line L2 and the abnormal line L3, and the current that is larger than that during the normal operation flows in the fuse 172, whereby the fuse 172 is blown. When the fuse 172 is blown, the supply of electric power to the load 111R from the power supply 40 is irreversibly disabled so that the controller 51 cannot resume the supply of electric power.

Note that in an alternative aspect to the above-described aspect, in the second mode, the first switch 175 may be turned off and the second switch 177 may be turned on. Even in such a case, when the resistance value of the second electric resistor 176 is sufficiently smaller than the resistance value of the first electric resistor 174, the current that is larger than that during the normal operation flows in the fuse 172, whereby the fuse 172 can be blown.

Note that it is sufficient that the resistance value of the first electric resistor 174 and the resistance value of the second electric resistor 176 are set so that the fuse 172 is not blown in the first mode and the fuse 172 is blown in the second mode.

The abnormal line L3 may be a so-called short-circuit line that does not include the second resistor 176 and has only conductive wire resistance of the lead wire.

In an alternative aspect to the aspect illustrated in FIG. 3 to FIG. 5, the disconnecting means 170 may be a means capable of performing only the first mode in which the supply of electric power to the load 111R from the power supply 40 is temporarily disabled so that the controller 51 can resume the supply of electric power. In this case, the disconnecting means 170 includes only a single switch, and therefore the disconnecting means 170 may not include the fuse 172.

Furthermore, the disconnecting means 170 may be a means capable of performing only the second mode in which the supply of electric power to the load 111R from the power supply 40 is irreversibly disabled so that the controller 51 cannot resume the supply of electric power. In this case, the disconnecting means 170 may not include the first switch 175.

As another example of the disconnecting means 170, a DC-DC converter may be used. To blow the fuse 172, the output current of the DC-DC converter is controlled so that the current equal to or larger than the current value which is required to blow the fuse 172 can flow in the fuse 172.

The flavor inhaler 100 may include a power supply degradation estimating means for estimating the degradation state (life) of the power supply 40. The power supply degradation detecting means may be any known means such as a current integration method, for example. As a specific example, the power supply degradation estimating means can estimate the degradation state of the power supply 40 by calculating a total integrated value of a current charged or discharged by the power supply 40. Note that instead of the current integration method, the power supply degradation estimating means may estimate the degradation state of the power supply 40 based on an increase in internal temperature of the power supply 40 and a change such as decreases in electric power value and voltage value output from the power supply 40 which are associated with an increase in impedance of the power supply 40.

The controller 51 may be configured to be capable of executing a plurality of operation modes. The operation modes include, for example, a power supply mode and a charge mode. The power supply mode is a mode in which electric power can be supplied to the load 111R from the power supply 40. The charge mode is a mode in which the charger 200 can charge the power supply 40.

The flavor inhaler 100 may include a detector 20 configured to detect an operation for using the load 111R. The detector 20 is preferably provided in the battery unit 112. A signal from the detector 20 can be detected by the controller 51.

The detector 20 may be an inhalation sensor configured to detect an inhalation from the mouthpiece of the flavor inhaler 100 by a user, for example. The inhalation sensor may be a MEMS (Micro Electro Mechanical Systems) sensor having a capacitor, and outputs a value indicating capacitance of the capacitor (for example, a voltage value) corresponding to differential pressure caused in the flow path by the inhaling operation. The output value may be recognized as a pressure or may be recognized as a flow rate per unit time or a flow velocity. Instead of the inhalation sensor, the detector 20 may be configured, for example, from a push button that detects when the user presses the button.

The flavor inhaler 100 may include a notification means 30. The notification means 30 is preferably provided in the battery unit 112. Examples of the notification means 30 include a light-emitting element like a LED, a voice and sound output device, and a sense feedback device like Haptics. When the sense feedback device is used as a notification means, the sense feedback device includes, for example, a vibrating element, and performs the notification by transmitting the vibration to the user. The controller 51 can control the notification means 30 to notify the user of a difference in operation mode of the flavor inhaler and an abnormality occurring in the flavor inhaler.

(Transition to Power Supply Mode or Charge Mode)

Figure 6:
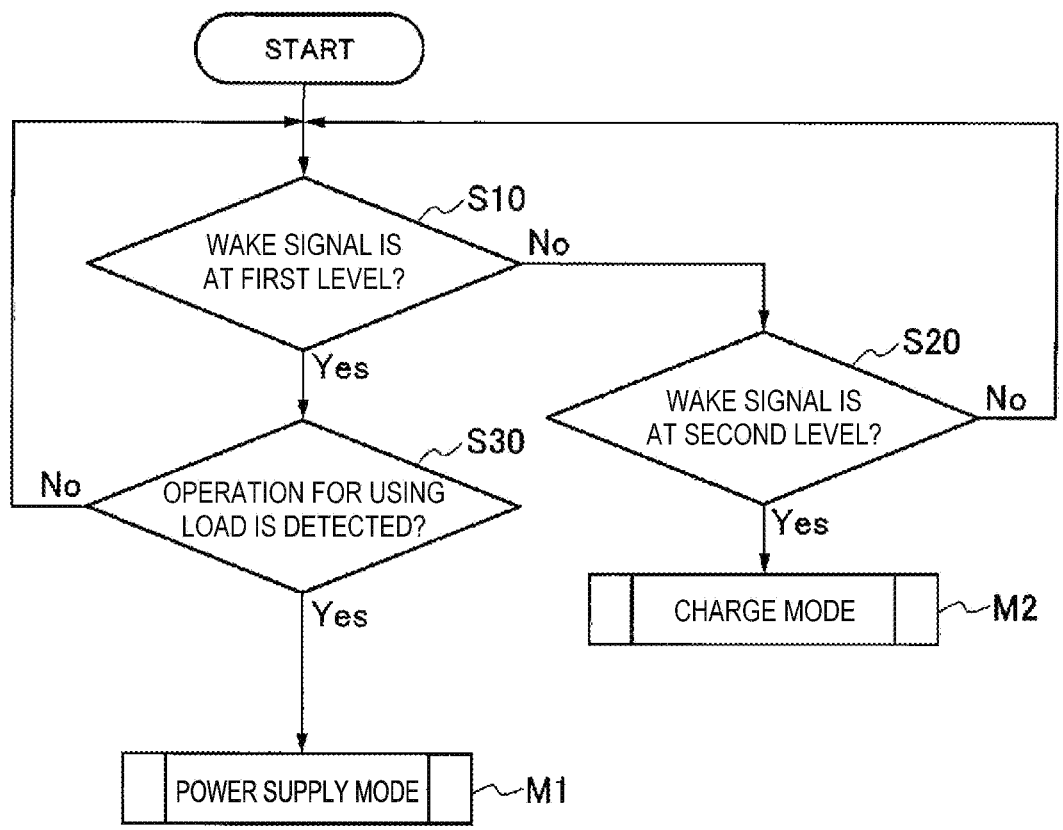
FIG. 6 is a flowchart illustrating a control flow to transition to a power supply mode and a charge mode.

FIG. 6 illustrates an example of a control flow to transition to a power supply mode M1 or a charge mode M2.

The controller 51 monitors a WAKE signal. When the WAKE signal is at the first level, the controller 51 proceeds the process to step S30 (step S10). The controller 51 determines whether the detector 20 detects the operation for using the load 111R (step S30). When the detector 20 detects the operation for using the load 111R (Yes in step S30), the controller 51 transitions the operation mode to the power supply mode M1. When the detector 20 does not detect the operation for using the load 111R (No in step S30), the controller 51 returns the process to step S10.

When the WAKE signal is at the second level, the controller 51 transitions the operation mode to the charge mode M2 (step S20).

Note that, although not limited to this example, the controller 51 may transition the operation mode to the power supply mode M1 based on any signal indicating that the load 111R is attached to the connection 120 of the battery unit 112. Similarly, the controller 51 may transition the operation mode to the charge mode M2 based on any signal indicating that the charger 200 is attached to the connection 120 of the battery unit 112.

(Power Supply Mode)

Figure 7:
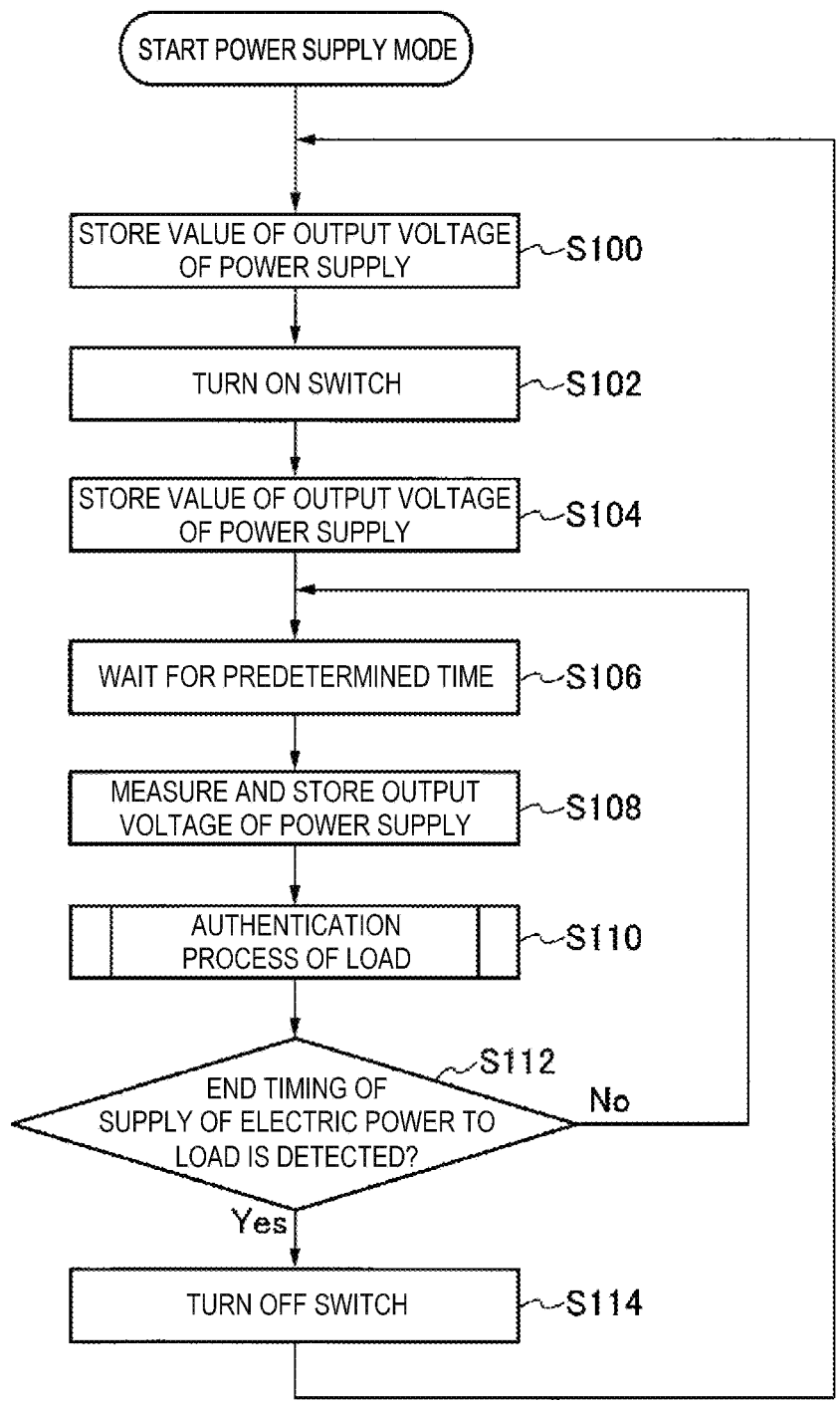
FIG. 7 is a flowchart illustrating a power supply mode according to one embodiment.

FIG. 7 is a flowchart illustrating a power supply mode according to one embodiment. When a first condition is satisfied in the power supply mode, the controller 51 turns on the switch 140 (step S102). When the switch 140 is turned on, the supply of electric power to the load 111R from the power supply 40 is started. The output voltage of the power supply 40 may be stored in the controller 51 (step S100) before the switch 140 is turned on. Note that the amount of electric power to be supplied to the load 111R from the power supply 40 may be optionally controlled. For example, the amount of electric power to be supplied to the load 111R from the power supply 40 may be adjusted by the pulse width control. The duty ratio with respect to the pulse width may be a value smaller than 100%. Note that the amount of electric power to be supplied to the load 111R from the power supply 40 may be adjusted by the pulse frequency control instead of the pulse width control.

In the present embodiment, the first condition may be a condition based on the detection of the operation for using the load 111R. As a specific example, the first condition may be that the operation for using the load 111R is detected. Specifically, the controller 51 turns on the switch 140 when the detector 20 detects the operation for using the load 111R. When the detector 20 is, for example, an inhalation sensor, the controller 51 turns on the switch 140 when the inhalation sensor detects the user's inhaling operation. When the detector 20 is a push button, the controller 51 turns on the switch 140 when the push button detects that the user presses the push button.

Instead of the above-described specific example, the first condition may be that the operation for using the load 111R is detected, and further another condition is satisfied. For example, when the detector 20 detects the operation for using the load 111R and the condition that the user presses the push button is satisfied, the controller 51 turns on the switch 140. As another example, when the detector 20 detects the operation for using the load 111R and the condition that the load 111R is authenticated is satisfied as described later, the controller 51 turns on the switch 140.

The output voltages of the power supply 40 are detected by the detector 160 at a predetermined time interval before the electric power is supplied to the load 111R (the power supply operates under a no-load condition) and while the electric power is supplied to the load 111R (the power supply operates under a load condition). The detected output voltages of the power supply 40 are stored in the controller 51 (steps S100, S104, S106, and S108). The output voltage of the power supply 40 that is detected by the detector 160 during the power supply mode M1 is stored in a memory provided in the controller 51.

In the present embodiment, during the power supply mode M1, the controller 51 may execute, based on the amount of change in the output voltage of the power supply 40 per a predetermined time period in the power supply mode M1, a specific control different from the supply of electric power to the load 111R. By way of example, the specific control may be, for example, an authentication process of the load 111R (step S110).

Figure 8:
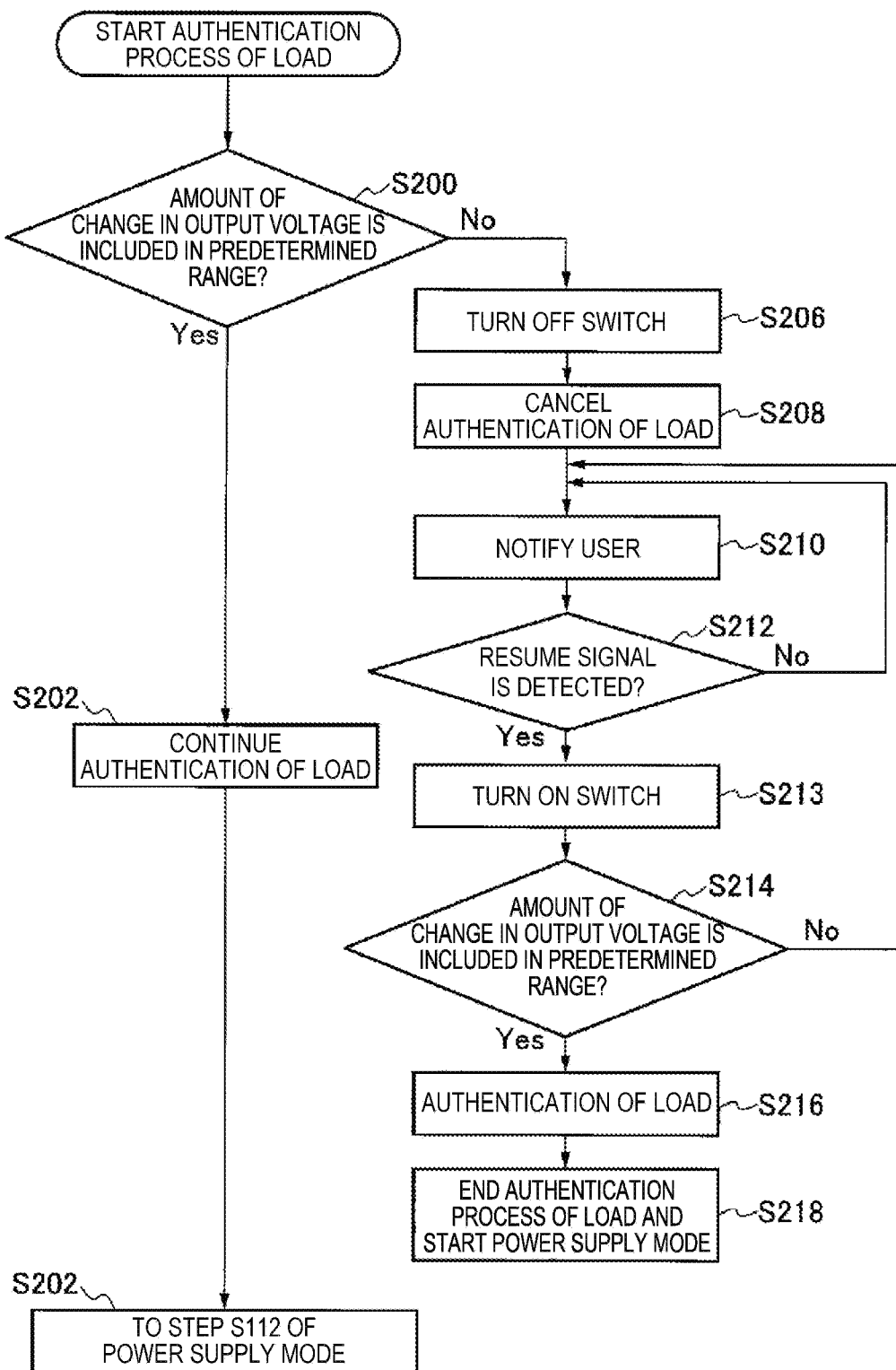
FIG. 8 is a flowchart illustrating an example of an authentication process of the load according to one embodiment.

As illustrated in FIG. 8, in the authentication process of the load 111R, specifically, the controller 51 determines whether the amount of change in the output voltage of the power supply 40 per a predetermined time period is included in a predetermined range (step S200). Here, it should be noted that the amount of change in the output voltage of the power supply 40 per a predetermined time period may correspond to a difference between the output voltage when the load 111R is energized and the output voltage when the load 111R is not energized.

When the amount of change in the output voltage of the power supply 40 per a predetermined time period is included in a predetermined range, the authentication of the load 111R is continued (step S202), and the process proceeds to step S112 in the power supply mode.

When the amount of change in the output voltage of the power supply 40 per a predetermined time period is not included in a predetermined range, the switch 140 is turned off (step S206), and the authentication of the load 111R is cancelled (step S208). When the authentication of the load 111R is cancelled, the controller 51 may notify the user of this fact (step S210). The notification to the user can be performed by the notification means 30.

In the state in which the authentication of the load 111R is cancelled, it is preferred that the controller 51 does not turn on the switch 140 even when the detector 20 detects the operation for using the load 111R, that is, that the electric power is not supplied to the load 111R.

After the authentication of the load 111R is cancelled, the controller 51 may execute the re-authentication process of the load 111R (step S214) when the resume operation (resume signal) is detected. Specifically, when detecting the resume signal (step S212), the controller 51 turns on the switch 140 (step S213), and detects the output voltage of the power supply 40 at a predetermined time interval. Then, when the amount of change in the output voltage of the power supply 40 per a predetermined time period is not included in a predetermined range, the notification to the user is performed (step S210) while keeping the authentication of the load 111R in the cancelled state. Note that when the switch is turned on in step S213 to detect the change in output voltage of the power supply 40, it is preferable to shorten the energization time or limit the electric power to be supplied to the load 111R from the power supply 40 by the pulse width control or the pulse frequency control, so that the aerosol source is not atomized by the current flowing in the load 111R. In other words, it is preferable to turn on the switch 140 for a short time so that the electric power smaller than the electric power to be supplied to the load 111R is supplied when the aerosol source is atomized in the power supply mode.

When the amount of change in the output voltage of the power supply 40 per a predetermined time period is included in a predetermined range, the load 111R is authenticated (step S216), the power supply mode is started. Here, it should be noted that the amount of change in the output voltage of the power supply 40 per a predetermined time period may correspond to a difference between the output voltage when the load 111R is energized and the output voltage when the load 111R is not energized after the resume signal is detected.

The resume operation (signal) may be a signal obtained by detecting that the load 111R is reconnected, a signal for detecting that the push button is pressed in a predetermined pattern, a signal obtained by detecting the inhaling operation in a predetermined pattern, a signal obtained by detecting the completion of one puff operation, or the like.

The authentication of the load 111R may be performed to determine whether the atomizing unit 111 connected to the battery unit 112 can be used, for example. In the above-described aspect, when the authentication of the load 111R is cancelled, for example, the controller 51 determines that the load 111R connected to the battery unit 112 cannot be used, and can prompt the replacement of the load 111R. When the amount of change in the output voltage of the power supply 40 per a predetermined time period exceeds the allowance range, for example, the controller 51 determines that the load 111R has been degraded, and can cancel the authentication to prompt the replacement of the load 111R. Alternatively, when an inauthentic atomizing unit having a voltage drop amount different from that of an authentic atomizing unit 111 is connected to the battery unit 112, the controller 51 cancels the authentication to prompt the replacement of the inauthentic load with the authentic load 111R.

In the authentication process of the load, when the authentication of the load 111R is continued (step S202), the process proceeds to step S112 of the power supply mode (see FIG. 7). In step S112, the controller 51 determines whether the end timing of the supply of electric power to the load 111R has been detected. When the end timing is detected, the controller 51 turns off the switch 140 to wait until the next supply of electric power to the load 111R is started while maintaining the power supply mode M1. When the above-described first condition is satisfied again, the controller 51 turns on the switch 140 (steps S100 and S102), and repeats the processes after steps S100 and S102.

The end timing of the supply of electric power to the load 111R may be the timing when it is detected that a predetermined time has elapsed since the supply of electric power to the load 111R was started. Alternatively, the end timing of the supply of electric power to the load 111R may be the timing when the detector 20 detects the completion of the operation for using the load 111R. When the detector 20 is, for example, an inhalation sensor, the end timing of the supply of electric power to the load 111R may be the timing when the inhalation sensor detects the completion of the user's inhaling operation.

(Predetermined Range)

The above-described predetermined range is set based on the normal voltage drop amount of the load 111R. Specifically, a lower limit value in the predetermined range may be set to a value smaller than a difference (voltage drop amount) between the voltage when the electric power is not supplied to the load 111R and the voltage when the electric power is supplied to the load 111R. Alternatively, the lower limit value in the predetermined range may be set to a value smaller than the decreasing amount of the output voltage of the power supply per a predetermined time period in the power supply mode in a state in which an authentic normal load 111R is connected to the connection 120. In this case, when the authentic normal load 111R is connected to the connection 120, the amount of change in the output voltage of the power supply is larger than the lower limit value in the predetermined range and therefore is included in the predetermined range, whereby the power supply mode can be continued.

On the other hand, when the inauthentic load or the severely degraded load is connected to the connection 120, the amount of change in the output voltage of the power supply tends to show a value different from that in the case where the authentic normal load 111R is connected to the connection 120. When the inauthentic load is used, for example, the amount of change in the output voltage of the power supply shows unique values because the resistance value of the inauthentic load itself is different from that of the authentic load and the contact failure occurs in the connection 120. The authentication of the inauthentic load can be cancelled if the predetermined range is set to exclude these unique values and to include the decreasing amount of the output voltage of the power supply per a predetermined time period in the power supply mode in the state in which the authentic normal load 111R is connected to the connection 120. The resistance value of the severely degraded load shows an abnormal value that is a value largely different from that of the normal load, although the authentic load is connected. The authentication of the severely degraded load can be cancelled if the predetermined range is set to exclude this abnormal value and to include the decreasing amount of the output voltage of the power supply per a predetermined time period in the power supply mode in the state in which the authentic normal load 111R is connected to the connection 120.

(Charge Mode)

Figure 9:
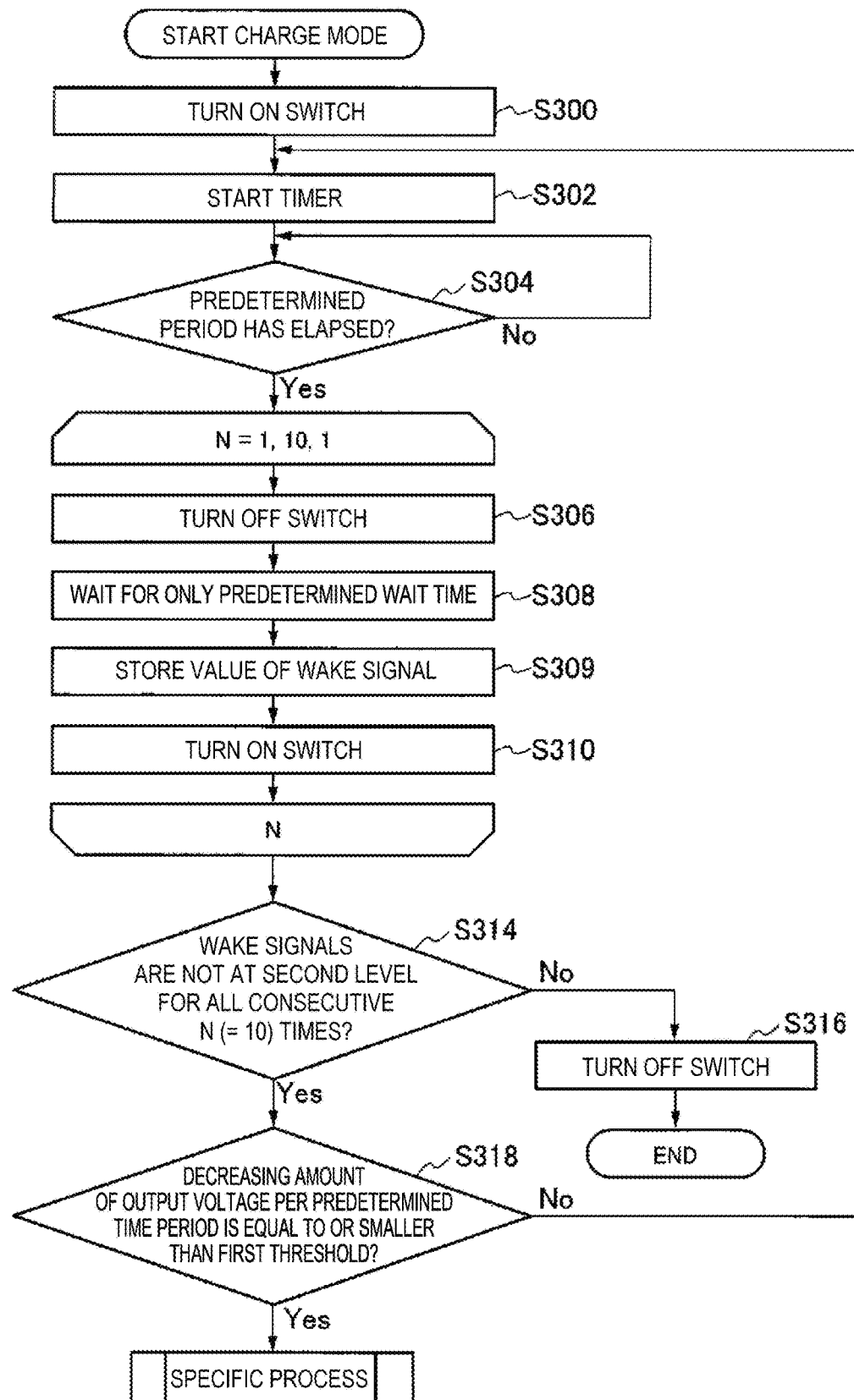
FIG. 9 is a flowchart illustrating the charge mode according to one embodiment.

FIG. 9 is a flowchart illustrating the charge mode according to one embodiment. It is preferred that the controller 51 turns on the switch when a second condition different from the above-described first condition is satisfied in the charge mode M2. That is, the conditions for turning on the switch are different between the charge mode and the power supply mode. Since the conditions for turning on the switch 140 are different between the charge mode and the power supply mode, malfunction can be easily suppressed.

The second condition may be a condition based on the connection of the charger 200 to the connection 120. The condition based on the connection of the charger 200 to the connection 120 may be a condition that a signal (second-level WAKE signal) indicating the connection of the charger 200 to the connection 120 has been detected. For example, the condition based on the connection of the charger 200 to the connection 120 may be a condition that the second-level WAKE signal has been detected once or consecutively a plurality of times.

Alternatively, the condition based on the connection of the charger 200 to the connection 120 may be a combination of a condition that a signal (second-level WAKE signal) indicating the connection of the charger 200 to the connection 120 has been detected and a condition that further another signal has been detected. Further another signal may be a signal for detecting when the user presses the push button, for example. Note that the push button may be provided on either the battery unit 112 or the charger 200, or on each of the battery unit 112 and the charger 200.

If the charger 200 is connected to the connection 120 of the battery unit 112 when the controller 51 turns on the switch 140, the current flows from the charger 200 to the power supply 40, whereby the power supply 40 is charged (step S300). The controller 51 turns on the switch 140, and starts the timer built in the battery unit (step S302). The timer is set to "zero" when started. The timer measures time from the start of the timer.

The controller 51 determines whether a predetermined time period has elapsed since the timer was started (step S304), and turns off the switch 140 when the predetermined time period has elapsed (step S306). This predetermined time period may be, for example, 100 ms.

When a predetermined wait time has elapsed since the controller 51 turned off the switch 140 (step S308), the controller 51 turns on the switch 140 again (step S310). Here, the predetermined wait time may be, for example, 400 μs. The controller 51 stores a value of the WAKE signal during the period between step S308 and step S310 (step S309).

The controller 51 repeats the processes from step S306 to step S310 a predetermined number of times. In the present embodiment, the predetermined number of times is 10 times. Next, the controller 51 determines whether the WAKE signals are at the second level for a predetermined consecutive number of times (here, 10 times) (step S314).

When the WAKE signals are not at the second level for the predetermined consecutive number of times, the controller 51 recognizes that the charger 200 is detached from the battery unit 112, turns off the switch 140 (step S316), and then ends a series of control flow. When the WAKE signal is at the second level at least once of the predetermined consecutive number of times, the controller 51 continues the charge mode M2.

Next, the controller 51 performs steps in which an abnormality in the charge mode is determined (step S318). Even when the controller 51 determines based on the WAKE signal that the charger 200 is connected to the connection 120, the determination may be wrong. For example, when the load 111R is attached to the connection 120, it is assumed that a malfunction is caused by a phenomenon such as chattering, which may cause erroneous transition to the charge mode M2. In step S318 in which an abnormality in the charge mode M2 is determined, it is assumed that the abnormality is determined in the case where the erroneous transition to the charge mode is thus caused.

Specifically, in the step in which abnormality in the charge mode is determined, when the decreasing amount of the output voltage of the power supply 40 per a predetermined time period in the charge mode M2 is equal to or smaller than a first threshold which is set based on the decreasing amount of the output voltage per the predetermined time period in the power supply mode M1, the controller 51 determines the abnormality in the charge mode. That is, in this case, the controller 51 estimates that the load 111R connected to the connection 120 is erroneously identified as the charger 200. In other words, the controller 51 determines that the charge mode is executed in a state in which the load 111R is connected to the connection 120. Note that the output voltage of the power supply 40 may be measured and stored at each predetermined interval.

Figure 11:
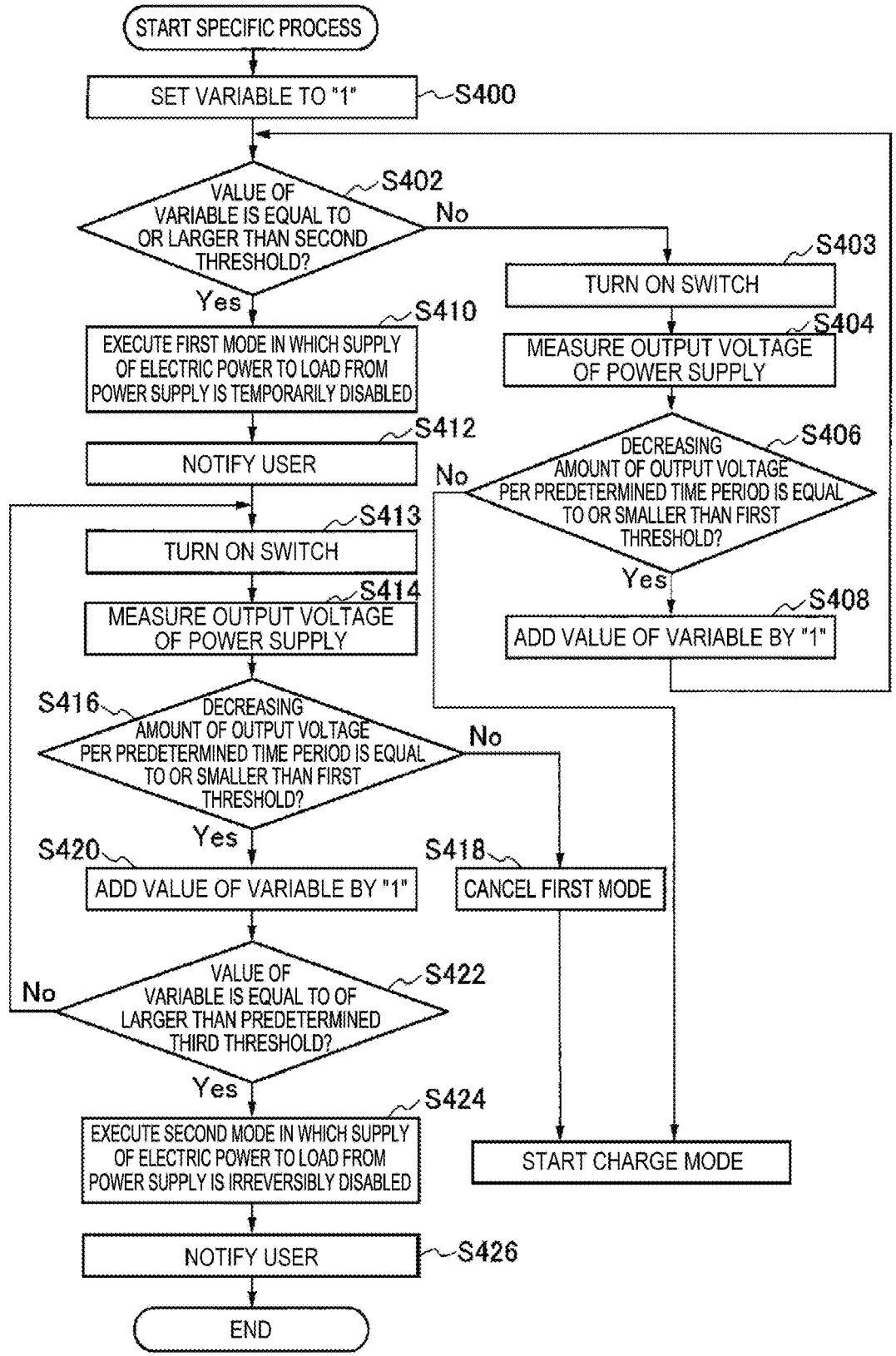
FIG. 11 is a flowchart illustrating an example of an abnormality process according to one embodiment.
Figure 12:
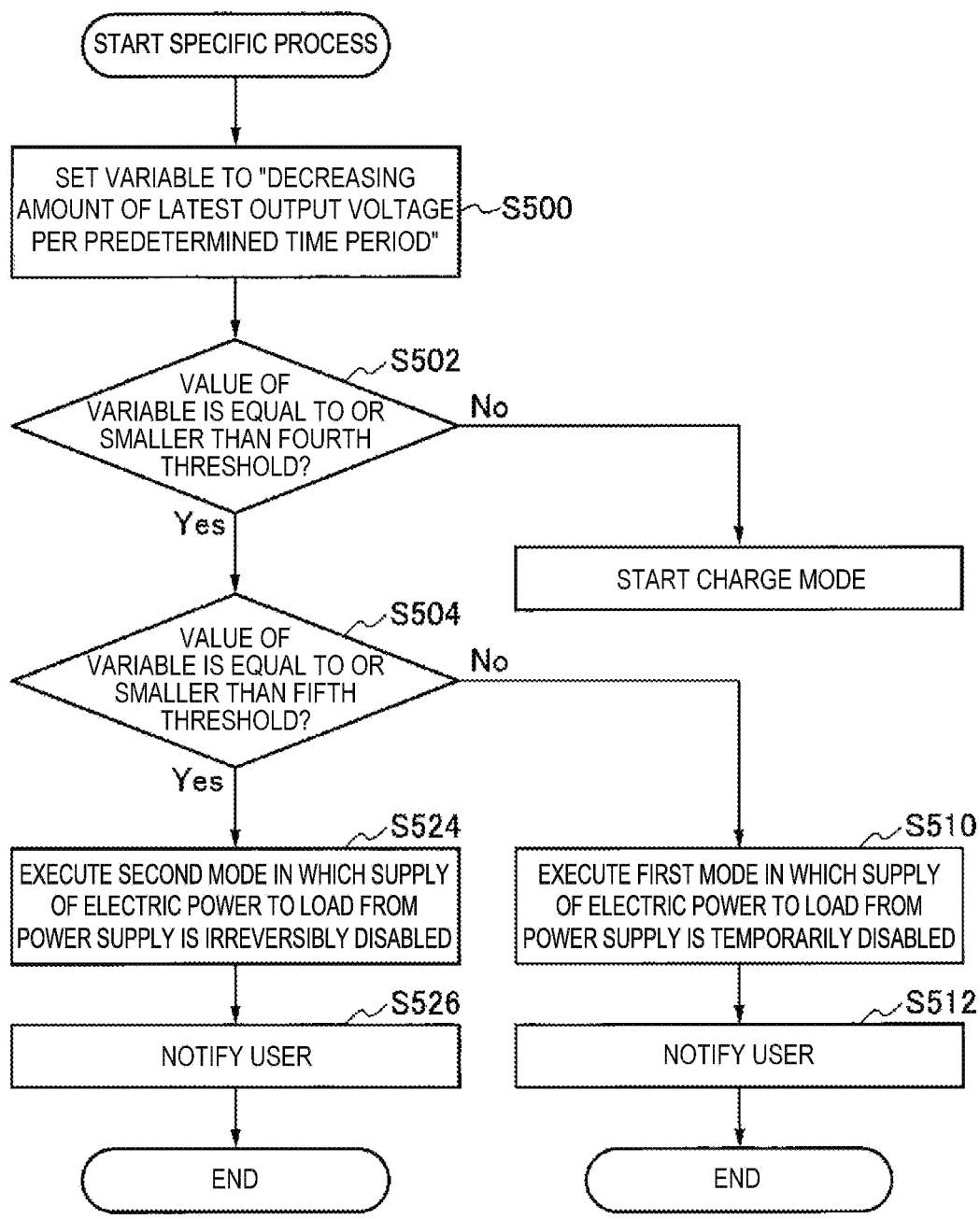
FIG. 12 is a flowchart illustrating another example of an abnormality process according to one embodiment.

When the controller 51 determines that the abnormality in the charge mode is present, the process proceeds to a specific process, for example, specific processes described later which is illustrated in FIG. 11 and FIG. 12. Alternatively, when the controller 51 determines that the abnormality in the charge mode is present, the controller 51 may stop the switch 140 and control the notification means to notify the user of the abnormality.

When the controller 51 determines that the abnormality in the charge mode is not present, the controller 51 continues the charge mode. Specifically, the controller 51 resets the timer to restart the timer, and repeats the processes after steps S302.

(First Threshold)

When the load 111R is connected to the connection 120, the output voltage of the power supply 40 per a predetermined time period when the switch 140 is turned on decreases according to the electric resistance value of the load 111R. On the other hand, when the charger 200 is connected to the connection 120, the output voltage of the power supply 40 per a predetermined time period is not ideally decreased. This is because when the charger 200 is connected to the connection 120, the power supply 40 is charged by the charger 200 or in a no-load condition, and the voltage between terminals of the power supply 40 increases in the former case, and the voltage between terminals of the power supply 40 is not ideally changed in the latter case. Accordingly, the first threshold may be equal to or smaller than the decreasing amount of the output voltage per a predetermined time period in the charge mode which is executed in a state in which the charger 200 is connected to the connection 120.

Strictly, when the charger 200 is connected to the connection 120, the output voltage of the power supply 40 per a predetermined time period decreases according to the voltage drop due to the dark current naturally discharged from the power supply 40. In this case, the first threshold is preferably larger than a value corresponding to the voltage drop due to the dark current. Furthermore, the first threshold is preferably set in consideration of an error of the detected output voltage value.

When the erroneous transition to the charge mode is caused although the load 111R is connected, the electric power larger than the electric power to be supplied to the load 111R in the power supply mode M1 may be supplied to the load 111R. In this case, the decreasing amount of the output voltage per a predetermined time period becomes smaller than the decreasing amount of the output voltage per a predetermined time period in the power supply mode. Taking this into account, the first threshold may be set to the value equal to or smaller than the decreasing amount of the output voltage per a predetermined time period in the power supply mode.

The first threshold may be set in advance in manufacturing the battery unit 112. Note that the first threshold is not necessarily maintained at the permanently preset value.

Figure 10:
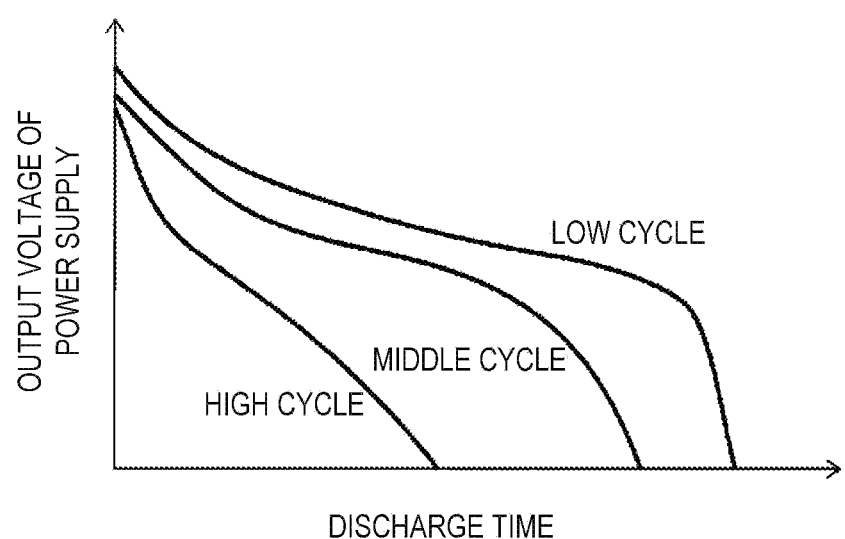
FIG. 10 is a graph showing an example of a relationship between degradation of a power supply and an output voltage of the power supply.

By way of example, the first threshold may be changed according to the degradation of the power supply 40 and the charge and discharge history of the power supply 40. Specifically, as shown in FIG. 10, typically, when the power supply 40 is degraded, that is, the number of charge/discharge cycles is increased, the output voltage of the power supply 40 decreases and the voltage drop amount increases. This is caused by decrease in the storage capacity due to the irreversible decomposition of electrolyte, and increase in the internal resistance caused by the change in the electrode structure due to aggregation of active material and electrically conductive assistant material. Accordingly, when the load 111R is connected to the connection 120, the power supply 40 is degraded and the decreasing amount of the output voltage of the power supply 40 in the predetermined period is reduced. Taking this into account, the accuracy in determination of the abnormality in the charge mode can be improved by appropriately changing the first threshold according to the degradation of the power supply 40.

Specifically, it is preferred that the first threshold is reduced as the power supply 40 is degraded. Typically, the decreasing amount of the output voltage in the predetermined period when the load 111R is connected to the connection 120 is increased as the power supply 40 is degraded. Accordingly, even when the first threshold is further reduced, the abnormality in the charge mode can be determined. On the other hand, a drawback in which the decreasing amount of the output voltage of the power supply 40 in the predetermined period which is detected in the charge mode falls below the first threshold due to, for example, an error of the detected value of the output voltage although the charger 200 is connected to the connection 120 can be suppressed by reducing the first threshold.

Note that when a lithium ion secondary battery is used for the power supply 40, in the relatively early charge/discharge cycle as is generally known, SEI (Solid Electrolyte Interphase) originating from decomposition of electrolyte is formed to cover the surface of the negative electrode. Since this SEI stabilize the electrochemical reaction, improvement in the reduction of the output voltage of the power supply 40 in the predetermined period can be expected. In such a case as well, the accuracy in determination of the abnormality in the charge mode can be improved by changing the first threshold according to the charge and discharge history and the number of charges and discharges.

As further another example, the first threshold may be changed based on the decreasing amount of the output voltage per a predetermined time period in the power supply mode. As described above, the output voltage in the power supply mode is stored in the controller 51 at each predetermined interval. Accordingly, the decreasing amount of the output voltage per a predetermined time period in the power supply mode can be calculated using the stored output voltage of the power supply 40 in the power supply mode. The controller 51 can feed back, to the first threshold, the decreasing amount of the output voltage per a predetermined time period in the power supply mode. Thus, even when the atomizing unit 111 (load 111R) is replaced, the first threshold can be appropriately set based on the voltage drop value of the replaced new load 111R. Even when the power supply 40 is degraded and the voltage drop amount of the output voltage is increased, the voltage drop amount of the output voltage following the degradation of the power supply 40 can be reflected to the first threshold to be set, and therefore, the accuracy in determination of the abnormality in the charge mode can be improved.

The controller 51 determines the abnormality in the charge mode. Even when misdetection that the charger 200 is connected to the connection 120 occurs, although the load 111R is connected to the connection 120, the controller 51 can determine the misdetection. Therefore, the switch 140 in the battery unit 112 can be prevented from erroneously continuing to be turned on, and the wasting of the electric power of the power supply can be prevented.

Specific Example of Step S318 in which an Abnormality in the Charge Mode is Determined In the step in which abnormality in the charge mode is determined, when the decreasing amount of the output voltage per a predetermined time period in the charge mode is equal to or smaller than a threshold which is set based on the decreasing amount of the output voltage per the predetermined time period in the power supply mode, the controller 51 determines that the abnormality in the charge mode is present. The output voltage of the power supply 40 in the charge mode is detected at each predetermined interval to calculate the decreasing amount of the output voltage of the power supply per the predetermined time period in the charge mode.

By way of example, in step S318, the decreasing amount of the output voltage per a predetermined time period in the charge mode is calculated by a difference between the output voltage value in the latest detection and the output voltage value obtained in one time earlier detection than the latest detection. That is, in step S318, the first threshold is compared with the difference between the latest detection value and the value obtained in one time earlier detection than the latest detection. Note that the detection value to be compared with the latest detection value to obtain the difference therebetween is not necessarily a value obtained in one time earlier detection than the latest detection, and a value obtained in two or more time earlier detection than the latest detection may be used to obtain the difference. In addition, the detection value obtained before the switch 140 is turned on to start the charge mode (prior to execution of step S300) may be used.

As another example, the decreasing amount of the output voltage per a predetermined time period in the charge mode may be defined by a predicted value derived from a plurality of output voltage values of the power supply which are detected at predetermined intervals, that is a predicted value obtained from an approximation straight line or an approximation curve. For example, the decrease in the output voltage can approximate the straight line by the least square method based on the plurality of output voltage values of the power supply which are detected at predetermined intervals, to calculate a predicted value of the decreasing amount of the output voltage per a predetermined time period in the charge mode based on the approximation straight line. The number of data (output voltage values) for using the least square method is optional, but it is preferred that the number is large so that an influence of the detection error will be sufficiently reduced. Thus, when the decreasing amount of the output voltage per a predetermined time period in the charge mode is derived from the predicted value obtained from the approximation straight line or the approximation curve, the influence of the detection error can be reduced because the gradient of the approximation straight line and the derivative value of the approximation curve having values other than "zero" are likely to result from the dark current due to self-discharge of the power supply 40 in a no-load condition.

As further another example, in step S318, the decreasing amount of the output voltage per a predetermined time period in the charge mode may be changed differently when the number of detecting the output voltage with reckoning from the start of the charge mode below a predetermined number and when the number of detecting the output voltage with reckoning from the start of the charge mode is equal to or above the predetermined number. For example, when the number of detecting the output voltage with reckoning from the start of the charge mode below a predetermined number, as described above, the decreasing amount of the output voltage per a predetermined time period in the charge mode may be calculated by a difference between the output voltage value in the latest detection and the output voltage value obtained in one time earlier detection than the latest detection. Note that when the number of detecting the output voltage with reckoning from the start of the charge mode is equal to or above the predetermined number, the decreasing amount of the output voltage per a predetermined time period in the charge mode may be calculated by a difference between the output voltage value in the latest detection and a predicted value obtained based on a plurality of output voltage values detected from the start of the charge mode. The predicted value is obtained using, for example, the least square method as described above.

Regarding the predetermined number, when the predicted value is used, the accuracy of the predicted value is improved as the number of data (output voltage values) for using the least square method increases. As is generally known, this is because in the least square method, the deviation between actual data and the approximation straight line or the approximation curve has a property of decreasing in proportion to the inverse square root of the number of data. Therefore, the predetermined number is optional, but it is preferred that the number is large so that an influence of the detection error of the output voltage will be sufficiently reduced. Thus, in the determination in step S318, the influence of the detection error of the output voltage of the power supply can be suppressed.

As another example, without the above-described approximation straight line and approximation curve, the gradient is derived from the plurality of output voltage values of the power supply which are detected at predetermined intervals, and this gradient may be used for the decreasing amount of output voltage per a predetermined time period in the charge mode. Alternatively, the decreasing amount of output voltage of the power supply per a predetermined time period in the charge mode may be estimated based on the moving average value derived from the plurality of output voltage values.

Specific Example 1 of Specific Process

When determining that the abnormality in the charge mode is present in step S318 in which an abnormality in the charge mode is determined, the controller 51 performs a specific process at least selectively executable to at least temporarily disable the supply of electric power to the load 111R from the power supply 40 (FIG. 11). FIG. 11 illustrates an example of such a specific process.

When the specific process is started, the value of a specific variable is set to "1" (step S400). In this example, the specific variable represents the number of times that the specific condition is satisfied. In this example, the specific condition is a condition that the decreasing amount of the output voltage per a predetermined time period in the charge mode is equal to or smaller than the above-described first threshold.

Next, the controller 51 determines whether the value of the specific variable is equal to or larger than the second threshold (step S402). The second threshold may be an arbitrary natural number of one or greater. By way of example, the second threshold may be "1." Alternatively, the second threshold may be a natural number of two or greater. In this case, in the specific process, the controller 51 can recheck whether the load 111R is connected to the connection 120 before at least temporarily disabling the supply of electric power to the load 111R from the power supply 40. The recheck whether the load 111R is connected to the connection 120 can be determined by whether the specific condition is satisfied again.

As a specific example, when the value of the specific variable is smaller than the second threshold, the controller 51 measures the output voltage of the power supply 40 (step S404), and calculates the decreasing amount of the output voltage per a predetermined time period again. Then, the controller 51 determines whether the above-described specific condition is satisfied, that is, whether the decreasing amount of the output voltage of the power supply 40 per a predetermined time period is equal to or smaller than the first threshold (step S406). Here, when the decreasing amount of the output voltage of the power supply 40 per a predetermined time period exceeds the first threshold, there is a possibility that the abnormality in the charge mode is not present. Therefore, the charge mode can be executed from the beginning. Instead of executing the charge mode from the beginning, the charge mode can be executed from some midpoint thereof if the decreasing amount of the output voltage of the power supply 40 per a predetermined time period is larger than the first threshold. By way of example, the process may be returned to step S302 of starting the timer in the charge mode.

On the other hand, when the decreasing amount of the output voltage of the power supply 40 per a predetermined time period is equal to or smaller than the first threshold, the value of the specific variable is increased by "1" (step S408), and the controller 51 determines whether the value of the specific variable is equal to or larger than the second threshold (step S402).

When the value of the specific variable is equal to or larger than the second threshold, the controller 51 temporarily determines that the abnormality in the charge mode is present, and executes the first mode in which the supply of electric power to the load 111R from the power supply 40 is temporarily disabled so that the controller 51 can resume the supply of electric power (step S410). Note that the first mode can be executed by controlling the above-described disconnecting means 170 by the controller 51. Then, the controller 51 notifies the user that the first mode is executed (step S412). The notification to the user can be performed by the notification means 30.

After executing the first mode, the controller 51 turns on the switch 140 and the switch 175 (step S413), measures the output voltage of the power supply 40 (step S414), and determines again whether the above-described specific condition is satisfied, that is, whether the decreasing amount of the output voltage of the power supply 40 per a predetermined time period is equal to or smaller than the first threshold (step S416). Note that after the notification to the user is performed (step S412), the controller 51 may measure the output voltage of the power supply 40 (step S414) if the resume operation (resume signal) is detected.

Here, when the decreasing amount of the output voltage of the power supply 40 per a predetermined time period exceeds the first threshold, there is a possibility that the abnormality in the charge mode is not present or that the abnormality has been resolved after the first mode is executed. Therefore, the first mode is cancelled (step S418), and the charge mode can be executed from the beginning. Instead of executing the charge mode from the beginning, the charge mode can be executed from some midpoint thereof.

On the other hand, when the decreasing amount of the output voltage of the power supply 40 per a predetermined time period is equal to or smaller than the first threshold, the value of the specific variable is increased by "1" (step S420), and the controller 51 determines whether the value of the specific variable is equal to or larger than a third threshold (step S422). The third threshold is a natural number larger than the second threshold. By way of example, the third threshold may be a natural number larger than the second threshold by "1."

When the value of the specific variable is smaller than the third threshold, the controller 51 measures the output voltage of the power supply 40 (step S414), and determines again whether the above-described specific condition is satisfied, that is, whether the decreasing amount of the output voltage of the power supply 40 per a predetermined time period is equal to or smaller than the first threshold (step S416).

When the value of the specific variable is equal to or larger than the third threshold, the controller 51 determines that the abnormality in the charge mode is present or it is difficult to resolve the abnormality, and executes the second mode in which the supply of electric power to the load 111R from the power supply 40 is irreversibly disabled so that the controller 51 cannot resume the supply of electric power (step S424). Note that the second mode can be executed by controlling the above-described disconnecting means 170 by the controller 51. Then, the controller 51 notifies the user that the second mode is executed (step S426). The notification to the user can be performed by the notification means 30.

As described above, the first condition (step S402) and the second condition (step S422) for determining whether the first mode and the second mode are to be executed respectively may be provided. In this case, the second condition is severer than the first condition. In other words, satisfying the second condition is more difficult than satisfying the first condition. For example, as in the case where the value of the specific variable is equal to or larger than the second threshold and smaller than the third threshold, in some cases the second condition cannot be satisfied even when the first condition is satisfied. When there is a possibility that the abnormality in the charge mode is present, the controller 51 executes the first mode in which the supply of electric power to the load from the power supply is temporarily disabled, and when there is a high possibility that the abnormality in the charge mode is present, the controller 51 executes the second mode in which the supply of electric power to the load from the power supply is irreversibly disabled.

Specific Example 2 of Specific Process

FIG. 12 illustrates another example of a specific process alternative to FIG. 11. When the specific process is started, the value of a specific variable is set to "the decreasing amount of the latest output voltage per a predetermined time period" (step S500). In this example, the specific variable includes the decreasing amount of the output voltage per a predetermined time period.

Next, the controller 51 determines whether the value of the specific variable is equal to or smaller than a fourth threshold (step S502). The fourth threshold may be the same as the above-described first threshold, for example, and may be set based on the decreasing amount of the output voltage of the power supply 40 per a predetermined time period in the power supply mode.

When the value of the specific variable is larger than the fourth threshold, there is a possibility that the abnormality in the charge mode is not present. Therefore, the charge mode can be executed from the beginning. Instead of executing the charge mode from the beginning, the charge mode can be executed from some midpoint thereof.

When the value of the specific variable is equal to or smaller than the fourth threshold, the controller 51 determines whether the value of the specific variable is equal to or smaller than a fifth threshold (step S504). Here, the fifth threshold is a value smaller than the fourth threshold. The fifth threshold may be set to, for example, a value below the lower limit of the decreasing amount of the output voltage of the power supply 40 per a predetermined time period when the authentic normal load 111R is used, or to for example, the decreasing amount of the output voltage of the power supply 40 per a predetermined time period when the power supply 40 is fully charged and the electric power is supplied to the load 111R at the duty ratio of 100%.

When the value of the specific variable is equal to or smaller than the fourth threshold and larger than the fifth threshold, the controller 51 temporarily determines that the abnormality in the charge mode is present, and executes the first mode in which the supply of electric power to the load 111R from the power supply 40 is temporarily disabled so that the controller 51 can resume the supply of electric power (step S510). Then, the controller 51 notifies the user that the first mode is executed (step S512).

When the value of the specific variable is equal to or smaller than the fifth threshold, the controller 51 determines that the abnormality in the charge mode is present, and executes the second mode in which the supply of electric power to the load 111R from the power supply 40 is irreversibly disabled so that the controller 51 cannot resume the supply of electric power (step S524). Then, the controller 51 notifies the user that the second mode is executed (step S526).

As described above, the first condition (step S502) and the second condition (step S504) for determining whether the first mode and the second mode are to be executed respectively may be provided. In this case, the second condition is severer than the first condition. In other words, satisfying the second condition is more difficult than satisfying the first condition. For example, as in the case where the value of the specific variable is equal to or smaller than the fourth threshold and larger than the fifth threshold, in some cases the second condition cannot be satisfied even when the first condition is satisfied.

(Timing of Control of Disconnecting Means)

In the above-described example, in the case where the charge mode is executed when the load 111R is connected to the connection 120, that is, where the load 111R connected to the connection 120 is erroneously identified as the charger 200, the controller 51 executes a specific process at least selectively executable to at least temporarily disable the supply of electric power to the load 111R from the power supply 40 (see FIG. 11 and FIG. 12).

Although not limited to this example, when detecting any abnormality in the load 111R or the power supply 40, the controller 51 may execute a specific process at least selectively executable to at least temporarily disable the supply of electric power to the load 111R from the power supply 40. Examples of abnormality in the load 111R or the power supply 40 include connection of an inauthentic load to the connection 120, use of the battery unit by an inauthentic user (cancel of user authentication), malfunction of the other battery unit, and the like. The connection of the inauthentic load to the connection 120 can be detected by, for example, the above-described authentication process of the load.

When the detector 20 is, for example, a push button, the user authentication can be performed by pressing the push button in a predetermined pattern. As another example, when the detector 20 is, for example, an inhalation sensor, the user authentication can be performed by pressing the user's inhaling operation in the predetermined pattern.

(Program and Storage Medium)

The above-described flows illustrated in FIGS. 6 to 9, FIG. 11 and FIG. 12 can be executed by the controller 51. That is, the controller 51 may include a program causing the battery unit 112 and the flavor inhaler 100 to execute the above-described method, and a storage medium storing therein the program.

Second Embodiment

Figure 13:
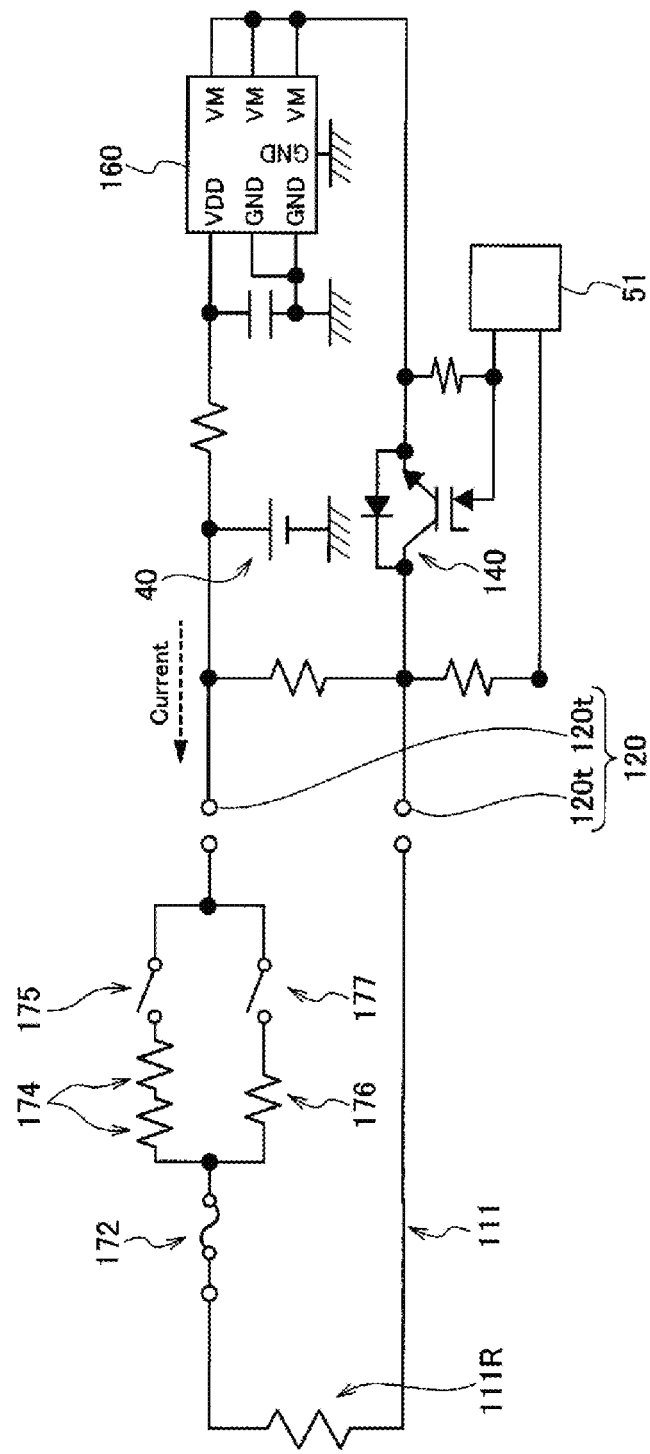
FIG. 13 is a diagram illustrating an electric circuit of a flavor inhaler according to a second embodiment.

Next, a flavor inhaler according to a second embodiment will be described with reference to FIG. 13. Note that the same components as those in the above-described embodiment are denoted by the same reference numerals, and the description thereof will be omitted. Hereinafter, the configuration different from the above-described embodiment will be described in detail.

In the present embodiment, the above-described disconnecting means 170 is provided in the atomization assembly 111, that is, the load 111R, not in the battery unit 112. The first switch 175 and the second switch 177 forming the disconnecting means 170 may be configured to be electrically connected with the controller 51 through an electric terminal (not illustrated). When the load 111R is connected to the connection terminals 120t, the controller 51 is configured to be able to control the first switch 175 and the second switch 177 of the disconnecting means 170. Thus, the controller 51 can execute specific processes illustrated in FIG. 11 and FIG. 12.

According to the present embodiment, when the controller 51 executes the second mode in which the supply of electric power to the load 111R from the power supply 40 is irreversibly disabled so that the controller 51 cannot resume the supply of electric power, the load 111R, that is, the atomization assembly 111 is replaced with new one, whereby the flavor inhaler 100 can be returned to the usable state. Typically, the atomization assembly 111 tends to be cheap relative to the battery unit 112 having expensive components such as the power supply 40. Accordingly, the present embodiment is advantageous particularly in terms of cost. The disconnecting means 170 may be provided to both of the battery unit 112 and the atomization assembly 111.

OTHER EMBODIMENTS

The present invention has been described by the above-described embodiments, but it should not be understood that the description and drawings constituting a part of the present disclosure limit the present invention. Various alternative embodiments, examples and operation techniques will become apparent for those skilled in the art from this disclosure.

For example, configurations described in each of the above-described embodiments may be combined and/or rearranged as much as possible.

The invention claimed is:

1. An apparatus configured to supply power for an aerosol inhaler comprising:
   a housing,
   a battery;
   a connection configured to be detachably connected to an atomization assembly for atomizing an aerosol source,
   a sensor configured to detect an inhalation of a user, and
   a controller configured to
      control supplying power from the battery to the atomization assembly when the connection is connected to the atomization assembly; and
      execute an authentication process to authenticate the atomization assembly, wherein
   the battery, the sensor and the controller are contained within the housing,
   the controller is configured to execute the authentication process on the atomization assembly when power is being supplied from the battery to the atomization assembly,
   the connection includes a plurality of terminals, and
   the controller is configured to
      identify whether the connection is connected to the atomization assembly based on a difference in electric potential between the plurality of terminals; and
      control supplying power from the battery to the atomization assembly when it is identified that the connection is connected to the atomization assembly and a signal output from the sensor indicates that an inhalation operation is being performed by the user.

2. An apparatus configured to supply power for an aerosol inhaler comprising:
   a housing;
   a battery;
   a connection configured to be detachably connected to an atomization assembly for atomizing an aerosol source;
   a sensor configured to detect an inhalation of a user; and
   a controller configured to
      control supplying power from the: battery to the atomization assembly when the connection is connected to the atomization assembly; and
      execute an authentication process to authenticate the atomization assembly, wherein
   the battery, the sensor and the controller are contained within the housing,
   the controller is configured to execute the authentication process on the atomization assembly when power is being supplied from the battery to the atomization assembly, and
   the controller is configured to execute the authentication process by comparing a change in output voltage of the battery over a predetermined period to a predetermined range while power is being supplied from the battery to the atomization assembly.

3. An apparatus configured to supply power for an aerosol inhaler comprising:
   a housing;
   a battery;
   a connection configured to be detachably connected to an atomization assembly for atomizing an aerosol source;
   a sensor configured to detect an inhalation of a user; and
   a controller configured to control supplying power from the battery to the atomization assembl when the connection is connected to the atomization assembly; and execute an authentication process to authenticate the atomization assembly, wherein the battery, the sensor and the controller are contained within the housing, the connection includes a plurality of terminals, the controller is configured to identify whether the connection is connected to the atomization assembly based on a difference in electric potential between the plurality of terminals, and the controller is configured to
determine whether an inhalation operation is performed based on a signal output from the sensor, and
perform control to supply power from the battery to the atomization assembly when it is identified that the connection is connected to the atomization assembly and it is determined that the inhalation operation is performed.

4. The apparatus of claim 3, wherein
the controller is configured to execute the authentication process to authenticate the atomization assembly when it is identified that the connection is connected to the atomization assembly, it is determined that the inhalation operation is performed and power is being supplied from the battery to the atomization assembly.

5. An apparatus configured to supply power for an aerosol inhaler, the apparatus comprising:
a housing;
a battery;
a connection configured to be detachably connected to an atomization assembly for atomizing an aerosol source;
a sensor configured to detect an inhalation of a user; and
a non-transitory computer-readable medium including:
computer-program instructions, which when executed by a controller, cause the controller to
control supplying power from the battery to the atomization assembly when the connection is connected to the atomization assembly; and
execute an authentication process to authenticate the atomization assembly, wherein
the battery, the sensor and the controller are contained within the housing, and
the authentication process includes comparing an electrical resistance of a load of the atomization assembly with a predetermined range.

6. An apparatus configured to supply power for an aerosol inhaler, the apparatus comprising:
a housing;
a battery;
a connection configured to be detachably connected to an atomization assembly for atomizing an aerosol source;
a sensor configured to detect an inhalation of a user; and
a non-transitory computer-readable medium including:
computer-program instructions, which when executed b a controller, cause the controller to
control supplying power from the battery to the atomization assembly when the connection is connected to the atomization assembly; and execute an authentication process to authenticate the atomization assembly, wherein the battery, the sensor and the controller are contained within the housing, the connection includes a plurality of terminals, and the computer-program instructions, which when executed by the controller, cause the controller to
identify whether the connection is connected to the atomization assembly based on a difference in electric potential between the plurality of terminals; and
control supplying power from the battery to the atomization assembly when it is identified that the connection is connected to the atomization assembly and a signal output from the sensor indicates that an inhalation operation is being performed by the user.

7. The apparatus of claim 6, wherein
the computer-program instructions, when executed by the controller, cause the controller to execute the authentication process to authenticate the atomization assembly based on an electrical resistance of a load of the atomization assembly that is obtained while power is being supplied to the atomization assembly.

8. A method performed by an apparatus configured to supply power for an aerosol inhaler, the apparatus including a housing, a battery, a connection including a plurality of terminals configured to be detachably connected to an atomization assembly for atomizing an aerosol source, and a sensor configured to detect an inhalation of a user, the method comprising:
determining, by a controller of the apparatus, whether the connection is connected to the atomization assembly based on a difference in electric potential between the plurality of terminals;
determining, by the controller, whether an inhalation operation is performed by a user based on a signal output by the sensor;
supplying power from the battery to the atomization assembly when it is determined that the connection is connected to the atomization assembly and the inhalation operation is performed by the user; and
executing an authentication process to authenticate the atomization assembly upon supplying power from the battery to the atomization assembly.

9. The method of claim 8, further comprising:
stopping power from being supplied from the battery to the atomization assembly when it is determined that the connection is connected to the atomization assembly, the inhalation operation is performed by the user and a result of the authentication process indicates that the atomization assembly is not authenticated; and
continuing to supply power from the battery to the atomization assembly when it is determined that the connection is connected to the atomization assembly, the inhalation operation is performed by the user and a result of the authentication process indicates that the atomization assembly is authenticated.

* * * * *